(12) United States Patent
Konry et al.

(10) Patent No.: US 11,066,697 B1
(45) Date of Patent: Jul. 20, 2021

(54) COLORIMETRIC AND MULTIPLEXED ISOTHERMAL RNA-BASED ASSAY FOR SARS-COV-2 AND OTHER VIRAL DIAGNOSTICS AND CELL ANALYSIS

(71) Applicant: Northeastern University, Boston, MA (US)

(72) Inventors: Tania Konry, Boston, MA (US); Ji Won Lim, Boston, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 16/911,280

(22) Filed: Jun. 24, 2020

Related U.S. Application Data

(60) Provisional application No. 63/003,237, filed on Mar. 31, 2020.

(51) Int. Cl.
  *C12Q 1/68* (2018.01)
  *C12Q 1/6837* (2018.01)
  *C12Q 1/70* (2006.01)
  *C12Q 1/6818* (2018.01)

(52) U.S. Cl.
  CPC ......... *C12Q 1/6837* (2013.01); *C12Q 1/6818* (2013.01); *C12Q 1/701* (2013.01); *C12Q 2600/16* (2013.01)

(58) Field of Classification Search
  CPC .................................................. C12Q 1/68
  See application file for complete search history.

(56) References Cited

U.S. PATENT DOCUMENTS

| | | | | |
|---|---|---|---|---|
| 9,745,617 | B2 * | 8/2017 | Larson | C12Q 1/6816 |
| 2014/0045712 | A1 * | 2/2014 | Link | C12Q 1/686 506/9 |
| 2015/0197804 | A1 * | 7/2015 | Willner | C12Q 1/6844 435/6.12 |

OTHER PUBLICATIONS

Qu et al., Ligation-Rolling Circle Amplification on Quantum Dot-Encoded Microbeads for Detection of Multiplex G-Quadruplex-Forming Sequences, Anal. Chem. 2018, 90, 20, 12051-12058 Publication Date: Sep. 26, 2018.*

Hamidi et al., Simple Rolling Circle Amplification Colorimetric Assay Based on PH for Target DNA Detection, Talanta 201 (Aug. 2019): 419-25.*

(Continued)

*Primary Examiner* — Aaron A Priest
(74) *Attorney, Agent, or Firm* — Verrill Dana, LLP

(57) ABSTRACT

Methods, devices, and kits for performing rapid, highly sensitive, high throughput, accurate, and flexible detection and quantification of nucleic acids based on highly optimized rolling circle amplification are provided. The methods, devices, and kits can be used to detect and track an emergent virus or other pathogen, including SARS-CoV-2, to test and diagnose individual patients with respect to a specific pathogen or disease, including COVID-19, and to detect and analyze cellular nucleic acids. The methods and devices also can be used to detect fragments and variants of DNA or RNA, including those present in cancer cells. The methods, devices, and kits are suitable for use in both high throughput screening carried out in centralized testing laboratories and in point-of-care testing devices used in the field, at home, in the workplace, or at public facilities for rapid detection and diagnosis.

14 Claims, 22 Drawing Sheets

Specification includes a Sequence Listing.

Number of multi-padlocks for better sensitivity

(56) References Cited

OTHER PUBLICATIONS

Dahl et al., Circle-to-circle amplification for precise and sensitive DNA analysis, Proc Natl Acad Sci USA. Mar. 30, 2004;101(13):4548-53. doi: 10.1073/pnas.0400834101. Epub Mar. 15, 2004.*

Ahmed et al., Concise Estimation for Detection of Coronavirus COVID19, Biomedical Journal of Scientific & Technical Research, Mar. 19, 2020, vol. 26, 4, pp. 20184-20185.*

Tang et al., Strand displacement-triggered G-quadruplex/rolling circle amplification strategy for the ultra-sensitive electrochemical sensing of exosomal microRNAs, Mikrochim Acta. Feb. 15, 2020;187(3):172. doi: 10.1007/s00604-020-4143-9.*

Liu et al., DNAzyme-Based Target-Triggered Rolling-Circle Amplification for High Sensitivity Detection of microRNAs, Sensors (Basel). Apr. 3, 2020;20(7):2017. doi: 10.3390/s20072017.*

Konry et al., Microsphere-based rolling circle amplification microarray for the detection of DNA and proteins in a single assay, Anal Chem. Jul. 15, 2009;81(14):5777-82. doi: 10.1021/ac900694y.*

Gomez et al., Visual detection of bacterial pathogens via PNA-based padlock probe assembly and isothermal amplification of DNAzymes, Dec. 16, 2014;86(24):11992-8. doi: 10.1021/ac5018748. Epub Dec. 2, 2014.*

Gu et al., Research Progress on Rolling Circle Amplification (RCA)-Based Biomedical Sensing, Pharmaceuticals (Basel). Apr. 21, 2018; 11(2):35. doi: 10.3390/ph11020035.*

De la Faverie et al., "Thioflavin T as a fluorescence light-up probe for G4 formation", Nucleic Acids Research, 2014, vol. 42, No. 8; doi: 10.1093/nar/gku111.

Konry et al., "Ultrasensitive detection of low-abundance surface-marker protein using isothermal rolling circle amplification in a microfluidic nano-liter platform", Small. Feb. 7, 2011;7(3):395-400. doi: 10.1002/smll.201001620.

Ida et al., "G-Quadruplexes as an Alternative Recognition Element in Disease-Related Target Sensing", Molecules 2019, 24, 1079; doi: 10.3390/molecules24061079.

Schwietzer et al., "Immunoassays with rolling circle DNA amplification: A versatile platform for ultrasensitive antigen detection", PNAS Aug. 29, 2000, vol. 97 No. 18 10113-10119; DOI: 10.1073/pnas.170237197.

Konry et al., "Target DNA detection and quantitation on a single cell with single base resolution", Technology (Singap World Sci). Sep. 2013; 1(1): 88; doi: 10.1142/S2339547813500088.

Li et al., "Stand-Alone Rolling Circle Amplification Combined with Capillary Electrophoresis for Specific Detection of Small RNA", Anal. Chem. 2009, 81, 12, 4906-4913; doi.org/10.1021/ac900578a.

Lizardi et al., "Mutation detection and single-molecule counting using isothermal rolling-circle amplification", Nature Genetics, vol. 19, Jul. 1998, 225-232; doi.org/10.1038/898.

Jiang et al., "Amplified detection of DNA ligase and polynucleotide kinase/phosphatase on the basis of enrichment of catalytic G-quadruplex DNAzyme by rolling circle amplification", Biosensors and Bioelectronics, 55 (2014):133-138. doi: 10.1016/j.bios.2013.12.001.

Yin C., "Genotyping coronavirus SARS-CoV-2: methods and implications", Genomics 112 (2020) 3588-3596. doi: 10.1016/j.ygeno.2020.04.016.

Ke et al., "Colorimetric Nucleic Acid Testing Assay for RNA Virus Detection Based on Circle-to-Circle Amplification of Padlock Probes", Journal of Clinical Microbiology Dec. 2011, p. 4279-4285; DOI: 10.1128/JCM.00713-11.

Golberg et al., "Cloud-Enabled Microscopy and Droplet Microfluidic Platform for Specific Detection of *Escherichia coli* in Water", PLoS One. Jan. 2014, vol. 9, Issue 1, e86341. doi: 10.1371/journal.pone.0086341.

* cited by examiner

```
dNTP
A - green fluorescent
T
C
G - red fluorescent
```

AAAAAAACGCGAAAAAACGCGAAAAAACG

Virus 1 present

GGGGGGGATAT GGGGGGGATAT GGGGGGG

Virus 2 present

BEAD

BEAD

FIG. 1C

SARS-CoV-2 N Gene Target Sequences

```
                        N1                                       N2                                                    N3
5 ATGGGCTATATAAACGT

Design of Padlock Target Binding Sequences

| | | |
|---|---|---|
| N1 seq | 5' GCT ATA TAA ACG TTT TCG CTT TTC CGT TTA 3' | Ligation required DNA for N1 |
| | 3' CGA TAT ATT TGC AAA AGC GAA AAG GCA AAT 5' AAA CGT TTA TAT AGC 3' | |
| | 5' (Phos) - TAA ACG GAA AAG CGA XXX XXX XXX ...... XXX XXX XXX | |

| | | |
|---|---|---|
| N2 seq | 5' AGT CTA CTC TTG TGC AGA ATG AAT TCT CGT 3' | Ligation required DNA2 for N2 |
| | 3' TCA GAT GAG AAC ACG TCT TAC TTA AGA GCA 5' GCA CAA GAG TAG ACT 3' | |
| | 5' (Phos) - ACG AGA ATT CAT TCT XXX XXX ...... XXX XXX XXX | |

| | | |
|---|---|---|
| N3 seq | 5' AGC ACA AGT AGA TGT AGT TAA CTT TAA TCT 3' | Ligation required DNA2 for N3 |
| | 3' TCG TGT TCA TCT ACA TCA ATT GAA ATT AGA 5' ACA TCT ACT TGT GCT 3' | |
| | 5' (Phos) - AGA TTA AAG TTA ACT XXX XXX ...... XXX XXX XXX | |

*FIG. 4B*

DNAzyme-Forming Detection Sequence
GAA ACC CAT CCC GCC CAA CCC CAT CAA AAC CCA TCC CGC CCA ACC CG Single RNA + Single padlock $L_{Sensitivity}$ = number of target copies ($n_{target}$)
X number of padlock DNA ($n_{padlock}$)

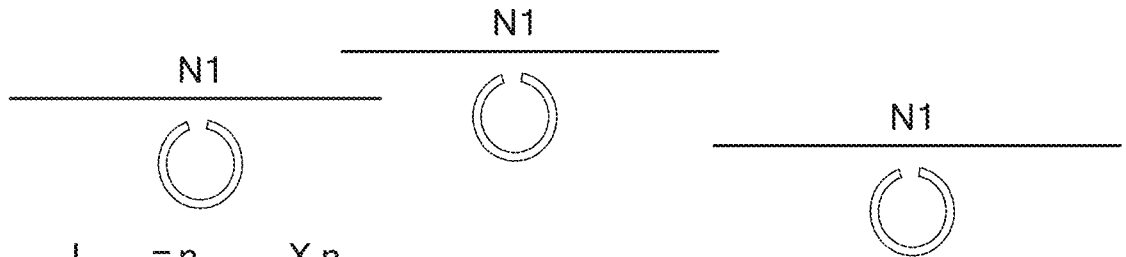

$L_{sen} = n_{target} \times n_{padlock}$ $L_{sen} = 3 \times 3 = 9$
= 3 copies X 3 corresponding padlocks

*FIG. 7A*

Single RNA + Multi-padlocks $L_{Sensitivity}$ = number of target copies ($n_{target}$) X [number of padlock DNA ($n_{padlock}$) X <u>number of hybridized regions to RNA (x)</u>]

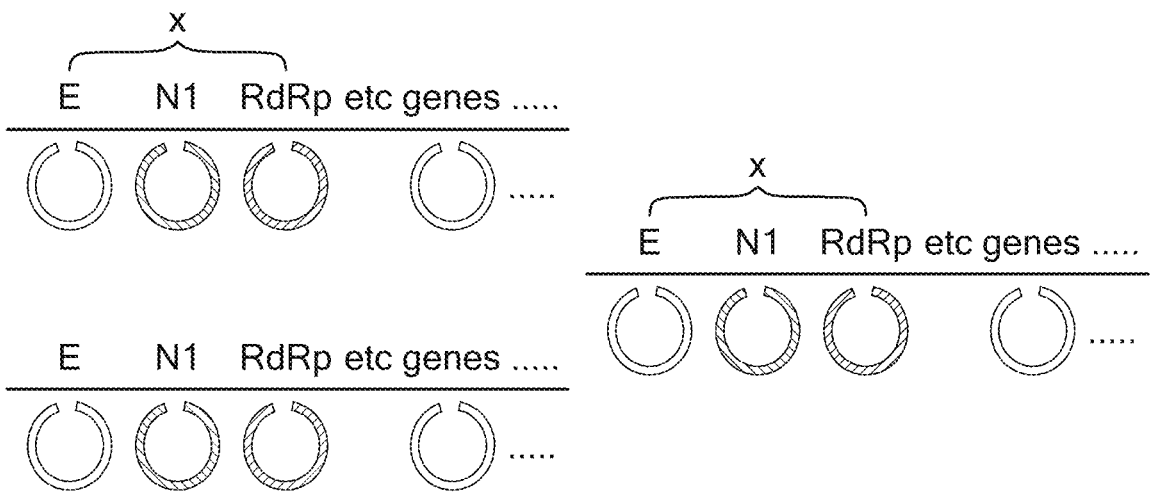

$L_{sen} = 3 \times (3 \times x) = 9x$
= 3 copies X (3 padlocks X x different region)

*FIG. 7B*

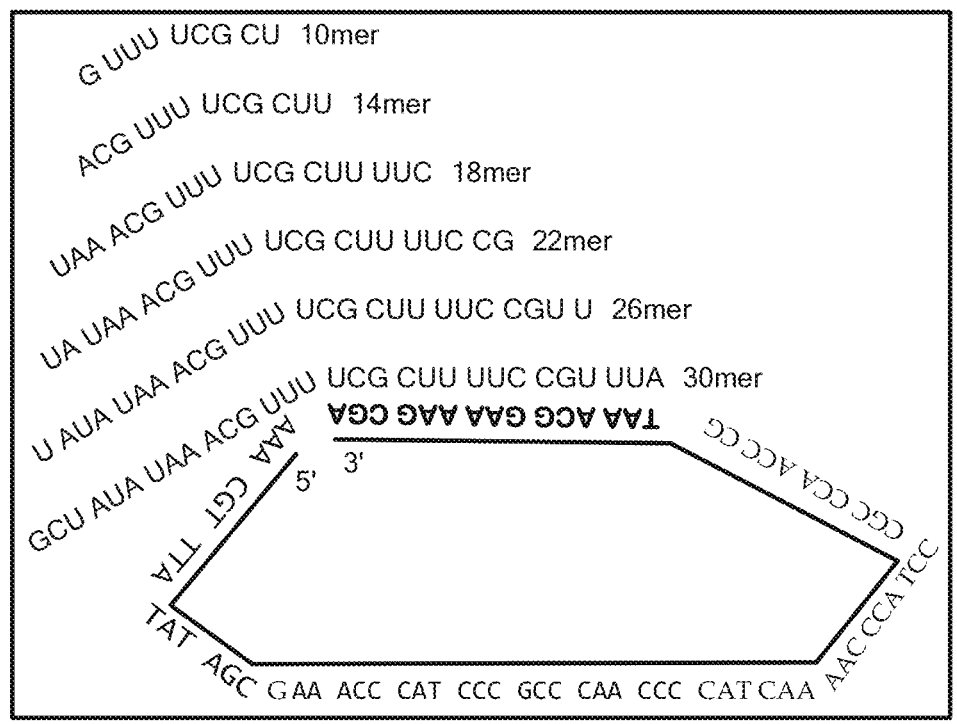
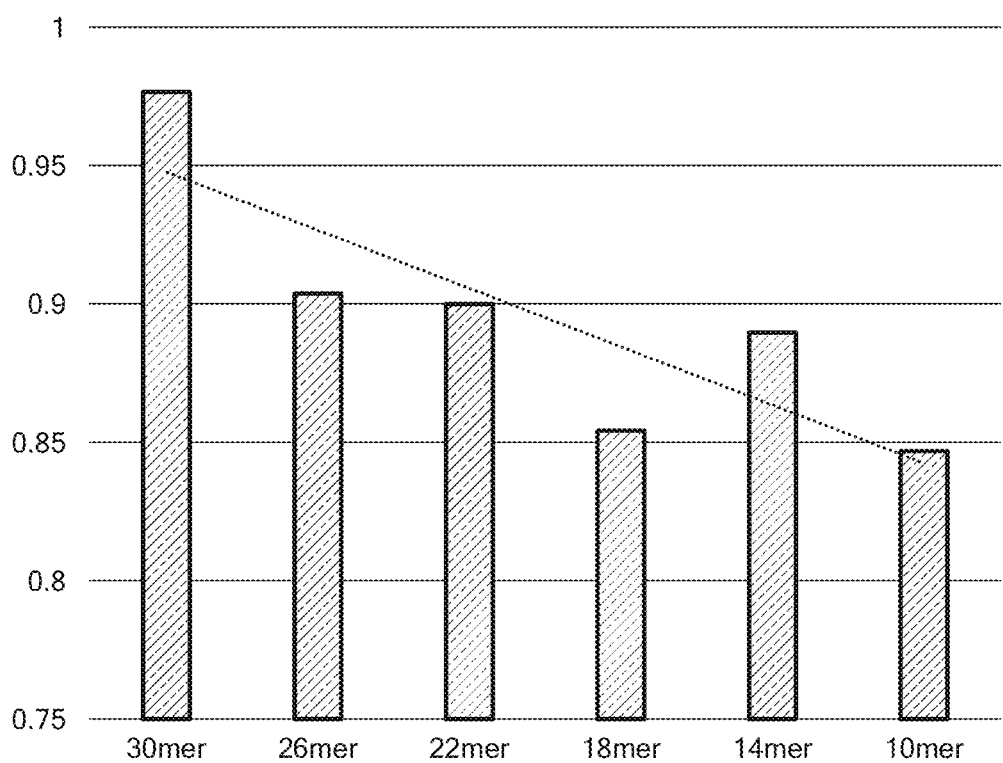
*FIG. 8A*

RdRp 1 (MN938385) 1~100 bp tgagttatga ggatcaagat gcact / tttcg catatacaaa acgtaatgtc atccctacta taactcaaat gaatc / ttaag tatgccatta gtgcaaagaa
RdRp - 1a AGTGC ATCTTGATCC gaaacccatcccgcccaaccccatcaaaacccatcccgcccaacccg TTTGTATATG CGAAA
RdRp - 1b GATTC ATTTGAGTTA gaaacccatcccgcccaaccccatcaaaacccatcccgcccaacccg TAATGGCATA CTTAA RdRp 2 (MN938385) 101~200 bp tagagctcgc accgtagctg gtgtc / tctat ctgtagtact atgaccaata gacagtttca tcaaaaatta ttgaa / atcaa tagccgccac tagaggagct
RdRp - 2a GACAC CAGCTACGGT gaaacccatcccgcccaaccccatcaaaacccatcccgcccaacccg AGTACTACAG ATAGA
RdRp - 2b TTCAA TAATT TTTGA gaaacccatcccgcccaaccccatcaaaacccatcccgcccaacccg GTGGCGGCTA TTGAT RdRp 3 (MN938385) 201~287 bp actgtagtaa ttgga / acaag caaattctat ggtggttggc acaacatgtt aaaaactgtt tatag / tgatg tagaaaaccc tcacctt
RdRp - 3a CTATA AACA GTTTTT gaaacccatcccgcccaaccccatcaaaacccatcccgcccaacccg GGGTTTTCTA CATCA
RdRp - 3b GCGCA GTAAGGATGG gaaacccatcccgcccaaccccatcaaaacccatcccgcccaacccg ACGCACACAA TCGAA S protein (MN938387) 107 bp S1 S2 S3
aatgtctatg cagat / tcatt tgtaattaga ggtgatgaa gtcagacaaa tcgct / ccagg gcaaactgga aagattgc tgattataat tataa / attac cagatgattt
S1 ATCTGCATAGACATT gaaacccatcccgcccaaccccatcaaaacccatcccgcccaacccgtaa TCTAATTACA AATGA
S2 AGCGATTTGTCTGAC gaaacccatcccgcccaaccccatcaaaacccatcccgcccaacccgtaa TCCAGTTTGCCCTGG
S2 TTATA ATTATAATCA gaaacccatcccgcccaaccccatcaaaacccatcccgcccaacccgtaa AAATCATCTG GTAAT To FIG. 9 continued

FIG. 9

From FIG. 9

M1 (NC_045512, gene ID=43740574, 1~120 bp)
atggcagatt ccaac/ggtac tattaccgtt gaagagctta aaaagctcct tgaacaatgg / caacctagtaa taggttcct attccttaca tggatttgtc ttcta/caatt tgcctatgcc
M1a    GTTGGAATCTGCCAT gaaaccatcccgcccaaccatcaaaaccatccgcccaaccgtaa AACGGTAATAGTACC
M1b    CCATGTTCAAGGAG gaaaccatcccgcccaaccatcaaaaccatccgcccaaccgtaa ACCTATTACTAGGTT
M1c    TAGAAGACAAATCCA gaaaccatcccgcccaaccatcaaaaccatccgcccaaccg

COLORIMETRIC AND MULTIPLEXED ISOTHERMAL RNA-BASED ASSAY FOR SARS-COV-2 AND OTHER VIRAL DIAGNOSTICS AND CELL ANALYSIS

CROSS REFERENCE TO RELATED APPLICATIONS

This application claims the priority of U.S. Provisional Application No. 63/003,237, filed on 31 Mar. 2020 and entitled "Multiplex Detection of Viral RNA by Rolling Circle Amplification", which is hereby incorporated by reference in its entirety.

BACKGROUND

Detection of pathogens such as emergent viruses is critically important in order to prevent disease spread and to prevent and control epidemics. This task is typically performed by conventional RT-PCR methods, which have several disadvantages, including lengthy analysis time and the need for complex thermocycling equipment and highly trained labor. Rolling circle amplification is an isothermal method which can be used to detect pathogen nucleic acids, but the existing methodology requires many steps and lacks adequate sensitivity for detecting the levels of nucleic acids found in patient samples. Thus, there is a need for improved detection of pathogen nucleic acids and cellular nucleic acids that is rapid, reliable, and easily carried out without specialized training.

SUMMARY

The present technology provides rapid, highly sensitive, high throughput, accurate, and flexible detection and quantification of nucleic acids. The methods and devices of the technology can be used to detect and track an emergent virus or other pathogen, to test and diagnose individual patients with respect to a specific pathogen or disease, and to detect and analyze cellular nucleic acids such as RNA in any desired situation. The methods and devices also can be used to detect fragments and variants of DNA or RNA. The technology also can be used to analyze the presence of bacteria, including novel bacterial species, in environmental samples or in the food chain, by detecting their ribosomal RNA, for example. The present technology is suitable for use in both high throughput screening carried out in centralized testing laboratories and in point-of-care testing devices used in the field or at home or the workplace for rapid detection and diagnosis.

An aspect of the technology is method of determining a presence, absence, or amount of a target nucleic acid molecule in a sample. The method includes the following steps: (a) providing (i) the target nucleic acid molecule, which contains at least one target sequence, (ii) an RCA initiation primer, (iii) one or more padlock probes; and (iv) nucleic acid ligase and polymerase enzymes; wherein, each padlock probe contains (1) a target binding sequence consisting of a pair of sequences complementary to adjacent portions of one of said target sequence, the pair forming termini of the padlock probe; (2) a primer binding sequence that is complementary to a padlock binding sequence of the RCA initiation primer; and (3) a detection sequence; wherein the RCA initiation primer contains said padlock binding sequence; (b) hybridizing the padlock probe with the target sequence and ligating the termini of the padlock probe using the ligase to form a circular single-stranded nucleic acid molecule; (c) hybridizing the circular single-stranded nucleic acid molecule to the RCA initiation primer; (d) extending the RCA initiation primer using the polymerase and the hybridized circular single-stranded nucleic acid molecule to form a single-stranded nucleic acid product containing a plurality of detection sequence copies; and (e) determining the presence, absence, or amount of the detection sequence copies resulting from step (d), wherein presence of the detection sequence copies indicates presence of the target nucleic acid molecule in the sample, absence of the detection sequence copies indicates absence of the nucleic acid molecule in the sample, and detection of an amount of the detection sequence copies indicates an amount of the target nucleic acid molecule in the sample.

Another aspect of the technology is a variant of the above described method, wherein the RCA reaction is circle-to-circle (C2C) RCA and further includes, between steps (c) and (d), the steps of: (c1) providing a plurality of C2C RCA primers that each contain a sequence complementary to the RCA initiation primer; (c2) fragmenting the single-stranded nucleic acid product using a restriction enzyme and restriction primer to obtain a plurality of linearized first circle products, each containing the detection sequence or a complement thereof; (c3) hybridizing the linearized first circle products to the C2C RCA primers and ligating the linearized first circle products using the ligase to form first circle products hybridized to the C2C RCA primers; (c4) extending the C2C RCA primers using the polymerase and the first circle products to obtain second single-stranded nucleic acid products; (c5) fragmenting the second single-stranded nucleic acid product using said restriction enzyme and restriction primer to obtain a plurality of linearized second circle products containing the detection sequence or a complement thereof; (c6) hybridizing the linearized second circle products to RCA initiation primers and ligating the linearized second circle products using the ligase to form second circle products hybridized to the RCA initiation primers; and proceeding to step (d), or optionally (c7) extending the RCA initiation primers using the polymerase and the second circle products to obtain further single-stranded nucleic acid products, each product containing a plurality of detection sequences or complements thereof, and repeating steps (c2)-(c6).

Yet another aspect of the technology is a kit for detecting a target nucleic acid molecule by RCA, the kit contains at least the following components: (i) an RCA initiation primer containing a padlock binding sequence; (ii) one or more padlock probes, each containing (1) a target binding sequence consisting of a pair of sequences complementary to adjacent portions of a target sequence within said target nucleic acid molecule, the pair forming termini of the padlock probe; (2) a primer binding sequence that is complementary to the padlock binding sequence of the RCA initiation primer; and (3) a detection sequence; (iii) a nucleic acid ligase, a nucleic acid polymerase, and optionally an exonuclease; and (iv) one or more reagents capable of producing a detectable product from the detection sequence or its complement.

Still another aspect of the technology is a kit for multiplex detection of two or more target nucleic acid molecules. The kit contains a plurality of different types of microbeads; wherein each type of microbead has a different first fluorescence emission and is coupled to a different RCA initiation primer; wherein each different RCA initiation primer hybridizes with a different set of padlock probes of the kit, the padlock probes hybridizing with a set of target sequences on a different nucleic acid molecule; and wherein the presence of each different nucleic acid molecule is indicated by a microbead having a different combination of first fluorescence emission and second fluorescence emission.

The technology can be further summarized in the following list of features.

1. A method of determining a presence, absence, or amount of a target nucleic acid molecule in a sample, the method comprising the steps of:

(a) providing (i) the target nucleic acid molecule, which comprises at least one target sequence, (ii) an RCA initiation primer, (iii) one or more padlock probes; and (iv) nucleic acid ligase and polymerase enzymes;

wherein, each padlock probe comprises (1) a target binding sequence consisting of a pair of sequences complementary to adjacent portions of one of said target sequence, the pair forming termini of the padlock probe; (2) a primer binding sequence that is complementary to a padlock binding sequence of the RCA initiation primer; and (3) a detection sequence;

wherein the RCA initiation primer comprises said padlock binding sequence;

(b) hybridizing the padlock probe with the target sequence and ligating the termini of the padlock probe using the ligase to form a circular single-stranded nucleic acid molecule;

(c) hybridizing the circular single-stranded nucleic acid molecule to the RCA initiation primer;

(d) extending the RCA initiation primer using the polymerase and the hybridized circular single-stranded nucleic acid molecule to form a single-stranded nucleic acid product comprising a plurality of detection sequence copies; and (e) determining the presence, absence, or amount of the detection sequence copies resulting from step (d), wherein presence of the detection sequence copies indicates presence of the target nucleic acid molecule in the sample, absence of the detection sequence copies indicates absence of the nucleic acid molecule in the sample, and detection of an amount of the detection sequence copies indicates an amount of the target nucleic acid molecule in the sample.

2. The method of feature 1 that does not include exonuclease treatment or purification of the circular single-stranded nucleic acid molecules after the ligation of step (b).

3. The method of feature 1, wherein at least 3, at least 10, at least 20, at least 30, at least 50, at least 100, or at least 500 padlock probes are used, each of the padlock probes comprising a target binding sequence complementary to a different target sequence of the target nucleic acid molecule.

4. The method of any of features 1-3, wherein the target nucleic acid molecule is derived from a viral genome, a viral genome transcript, a prokaryotic genome, a prokaryotic RNA, a eukaryotic cell genome, or a eukaryotic cell RNA.

5. The method of feature 4, wherein the target nucleic acid is from a virus selected from the group consisting of SARS-CoV-2, SARS, MERS, influenza, and ebola.

6. The method of any of features 1-5, wherein the presence, absence, or amount of the detection sequence copies is determined by colorimetric detection of a colored product generated by a chemical reaction carried out using the detection sequence copies.

7. The method of feature 6, wherein the detection sequence copies comprise a sequence that forms a G-quadruplex capable of forming a hemin-chelating DNAzyme that oxidizes a substrate with hydrogen peroxide to form a colored product.

8. The method of any of features 1-5, wherein the presence, absence, or amount of the detection sequences is determined by fluorescence detection of detection sequences or complements thereof labeled by inclusion of a fluorescently labeled base in the polymerase reaction of step (d), and wherein the detection sequences are enriched in said fluorescently labeled base.

9. The method of any of features 1-8 that is carried out using a microfluidic device, an array, a microwell plate, one or more tubes, or using a paperfluidic format.

10. The method of feature 9, wherein the method is carried out in multiplex format.

11. The method of any of features 1-10, wherein the RCA initiation primer is coupled to a solid support.

12. The method of feature 11, wherein the solid support is selected from microbeads, a glass surface, a polymer surface, a paper surface, or a surface in a tube, a chip, a microwell plate, or a microfluidic device.

13. The method of feature 12, wherein the solid support is microbeads, and the microbeads are docked in an array of a microfluidic device.

14. The method of feature 8, wherein a plurality of RCA initiation primers are attached to microbeads, wherein the microbeads emit a first fluorescence emission and the fluorescent detection sequences or detection sequence complements emit a second fluorescence emission that is separately detectable from the first fluorescence emission. and wherein the presence or amount of the target nucleic acid molecule is indicated by the presence or amount of both the first fluorescence emission and the second fluorescence emission at the microbeads.

15. The method of feature 14, wherein the method is carried out in a multiplex format capable of simultaneously detecting two or more target nucleic acid molecules using two or more types of microbeads, wherein each type of microbeads has a different first fluorescence emission and is coupled to a different plurality of RCA initiation primers, wherein each different plurality of RCA primers hybridizes with a different padlock probe or set of padlock probes comprising target binding sequences complementary to target sequences on a different target nucleic acid molecule, and wherein the presence or amount of each different target nucleic acid molecule is indicated by the presence or amount of a different combination of first and second fluorescence emissions at the microbeads.

16. The method of any of the preceding features, wherein the RCA reaction is circle-to-circle (C2C) RCA and further comprises, between steps (c) and (d), the steps of:

(c1) providing a plurality of C2C RCA primers that each comprise a sequence complementary to the RCA initiation primer;

(c2) fragmenting the single-stranded nucleic acid product using a restriction enzyme and restriction primer to obtain a plurality of linearized first circle products, each comprising the detection sequence or a complement thereof;

(c3) hybridizing the linearized first circle products to the C2C RCA primers and ligating the linearized first circle products using the ligase to form first circle products hybridized to the C2C RCA primers;

(c4) extending the C2C RCA primers using the polymerase and the first circle products to obtain second single-stranded nucleic acid products;

(c5) fragmenting the second single-stranded nucleic acid product using said restriction enzyme and restriction primer to obtain a plurality of linearized second circle products comprising the detection sequence or a complement thereof;

(c6) hybridizing the linearized second circle products to RCA initiation primers and ligating the linearized second circle products using the ligase to form second circle products hybridized to the RCA initiation primers; and proceeding to step (d), or optionally (c7) extending the RCA initiation primers using the polymerase and the second circle products to obtain further single-stranded nucleic acid products, each product comprising a plurality of detection sequences or complements thereof, and repeating steps (c2)-(c6).

17. The method of any of the preceding features, wherein the nucleic acid molecule is an RNA molecule from SARS-CoV-2 and said padlock probe comprises a sequence of at least 20 consecutive nucleotides complementary to any portion of the SARS-CoV-2 RNA molecule.

18. The method of any of the preceding features that is capable of detecting an amount of said target nucleic acid molecule in the femtomole range or in the attomole range.

19. The method of any of the preceding features that is carried out in less than four hours, in less than two hours, or in less than one hour.

20. The method of any of the preceding features that is used for detection of a viral infection in a subject by detecting the presence of said target nucleic acid molecule in a sample from the subject.

21. The method of feature 20, wherein the viral infection is COVID-19.

22. The method of feature 20 or 21 that is used to identify which viral infection a subject has by determining simultaneously the presence, absence, or amount of two or more different target nucleic acid molecules, each nucleic acid molecule specifically identifying a different virus.

23. The method of feature 22, wherein the presence, absence, or amount of RNA molecules from a SARS-CoV-2 strain and an influenza strain, from two or more different SARS-CoV-2 strains, or two or more different influenza strains are simultaneously determined.

24. A kit for detecting a target nucleic acid molecule by RCA, the kit comprising:

(i) an RCA initiation primer comprising a padlock binding sequence;

(ii) one or more padlock probes, each comprising (1) a target binding sequence consisting of a pair of sequences complementary to adjacent portions of a target sequence within said target nucleic acid molecule, the pair forming termini of the padlock probe; (2) a primer binding sequence that is complementary to the padlock binding sequence of the RCA initiation primer; and (3) a detection sequence;

(iii) a nucleic acid ligase, a nucleic acid polymerase, and optionally an exonuclease; and (iv) one or more reagents capable of producing a detectable product from the detection sequence or its complement.

25. The kit of feature 24, wherein the RCA initiation primer is coupled to a solid support.

26. The kit of feature 25, wherein the solid support is a plurality of microbeads.

27. The kit of feature 26 that is for multiplex detection of two or more target nucleic acid molecules, the kit comprising a plurality of different types of microbeads; wherein each type of microbead has a different first fluorescence emission and is coupled to a different RCA initiation primer; wherein each different RCA initiation primer hybridizes with a different set of padlock probes of the kit, the padlock probes hybridizing with a set of target sequences on a different nucleic acid molecule; and wherein the presence of each different nucleic acid molecule is indicated by a microbead having a different combination of first fluorescence emission and second fluorescence emission.

28. The kit of feature 27 further comprising a plurality of different nucleotides or oligonucleotides labeled with said second fluorescence emissions.

29. The kit of any of features 25-28, that is for detection of at least three different target sequences of said target nucleic acid molecule, the kit comprising at least three padlock probes, each comprising a different target binding sequence.

30. The kit of any of features 25-29 that is for use of C2C RCA, the kit further comprising a C2C RCA primer, a restriction enzyme, and a restriction primer.

31. The kit of feature 30, wherein the RCA initiation primer and the C2C RCA primer are coupled to a plurality of microbeads, and each microbead is coupled to both the RCA initiation primer and the C2C RCA primer.

32. The kit of any of features 24-26 or 29-31 that is for colorimetric detection of detectable product, the kit further comprising one or more reagents for producing a colored detectable product using the detection sequence.

33. The kit of any of features 24-32, further comprising a microfluidic device or chip.

34. The kit of any of features 24-33, comprising at least 3, at least 10, at least 30, at least 100, at least 300, or at least 500 of said padlock probes, each containing a different target binding sequence.

BRIEF DESCRIPTION OF DRAWINGS

FIG. 1C shows a variation of the process of FIG. 1B in which multiplex detection of the presence or absence of two different target molecules using a different padlock probe for each, wherein each padlock probe contains a detection sequence (SEQ ID NO:1 for Virus 1; SEQ ID NO:2 for Virus 2) enriched in a different nucleotide, allowing two different fluorescent labels to be used simultaneously and different colors of fluorescence to signal the two targets.

FIG. 2A shows a schematic illustration of the formation of aqueous microdroplets in a stream of oil, wherein the microdroplets entrap both the target nucleic acid and one or more microbeads linked to an RCA initiation primer. The microdroplets are captured in an array, where the RCA reaction is performed and colored and/or fluorescent product becomes detectable using imaging microscopy. FIG. 2B shows an actual microfluidic device loading microdroplets into an array for a process like that of FIG. 2A. FIG. 2C schematically depicts a top view of a docking array suitable for trapping either aqueous microdroplets or microbeads not present in droplets but dispersed in an aqueous stream of a microfluidic device. FIG. 2D shows schematically some possible points of attachment of RCA primers to surfaces within a portion of a microfluidic device shown in cross section.

In FIG. 3A the sample is loaded together with required enzymes and reagents, which diffuse toward a set of embedded microbeads that are conjugated to RCA primers, which become labeled through formation of a colored product or concentration of a fluorescent product on the beads in the presence of the target. FIGS. 3B and 3C show different configurations for performing multiplex assays.

FIG. 4A shows three sequences within the SARS-CoV-2 N gene (SEQ ID NO:3) and their corresponding sequences within the mRNA transcript (SEQ ID NO:4) of the gene. The highlighted N1 (SEQ ID NO:5), N2 (SEQ ID NO:8), and N3 (SEQ ID NO:11) sequences are suitable target sequences for detecting SARS-CoV-2. FIG. 4B shows the corresponding target-binding sequences (SEQ ID NOS:6,9, 12) of three padlock probes designed to detect the N gene of SARS-CoV-2 using an RCA assay. Each padlock probe has a 5' end target binding sequence and a 3' end target binding sequence, forming a pair which, when ligated, form a sequence complementary to the target sequence. The sequence "XXX XXX . . . XXX XXX XXX" refers to the remainder of each padlock probe, which joins the target binding sequences and contains a common RCA primer binding sequence and a common detection sequence. The padlock probe fragments are SEQ ID NO:7 (N1 probe), SEQ ID NO:10 (N2 probe), and SEQ ID NO:13 (N3 probe).

FIG. 7A shows a calculation of sensitivity using a single target sequence and single corresponding padlock probe. FIG. 7B shows a calculation of the sensitivity using multiple distinct target sequences and multiple corresponding padlock probes.

FIG. 8A shows the efficiency as a function of the length of the target binding sequence of a padlock probe. The graph shows ligated DNA concentration (µM) as a function of target RNA fragment length using the illustrated padlock DNA (target was N gene of SARS-CoV-2).

FIG. 9 shows a collection of padlock probe sequences for use in detection of SARS-CoV-2 using target sequences within the RdRp, S protein, M protein, and N protein transcripts. The transcripts are SEQ ID NO:21 (RdRp1), SEQ ID NO:24 (RdRp2), SEQ ID NO:27 (RdRp3), SEQ ID NO:30 (S protein), SEQ ID NO:34 (M1), SEQ ID NO:38 (M2), SEQ ID NO:42 (M3), SEQ ID NO:46 (N1), and SEQ ID NO:48 (N2), and the corresponding padlock probes are SEQ ID NO:22 (RdRp1a), SEQ ID NO:23 (RdRp1b), SEQ ID NO:25 (RdRp2a), SEQ ID NO:26 (RdRp2b), SEQ ID NO:28 (RdRp3a), SEQ ID NO:29 (RdRp3b), SEQ ID NO:31 (S1), SEQ ID NO:32 (S2), SEQ ID NO:33 (S3), SEQ ID NO:35 (M1a), SEQ ID NO:36 (M1b), SEQ ID NO:37 (M1c), SEQ ID NO:39 (M2a), SEQ ID NO:40, (M2b), SEQ ID NO:41 (M2c), SEQ ID NO:43 (M3a), SEQ ID NO:44 (M3b), SEQ ID NO:45 (M3c), SEQ ID NO:47 (N1), SEQ ID NO:49 (N2), and SEQ ID NO:51 (N3).

DETAILED DESCRIPTION

Figure 1A:
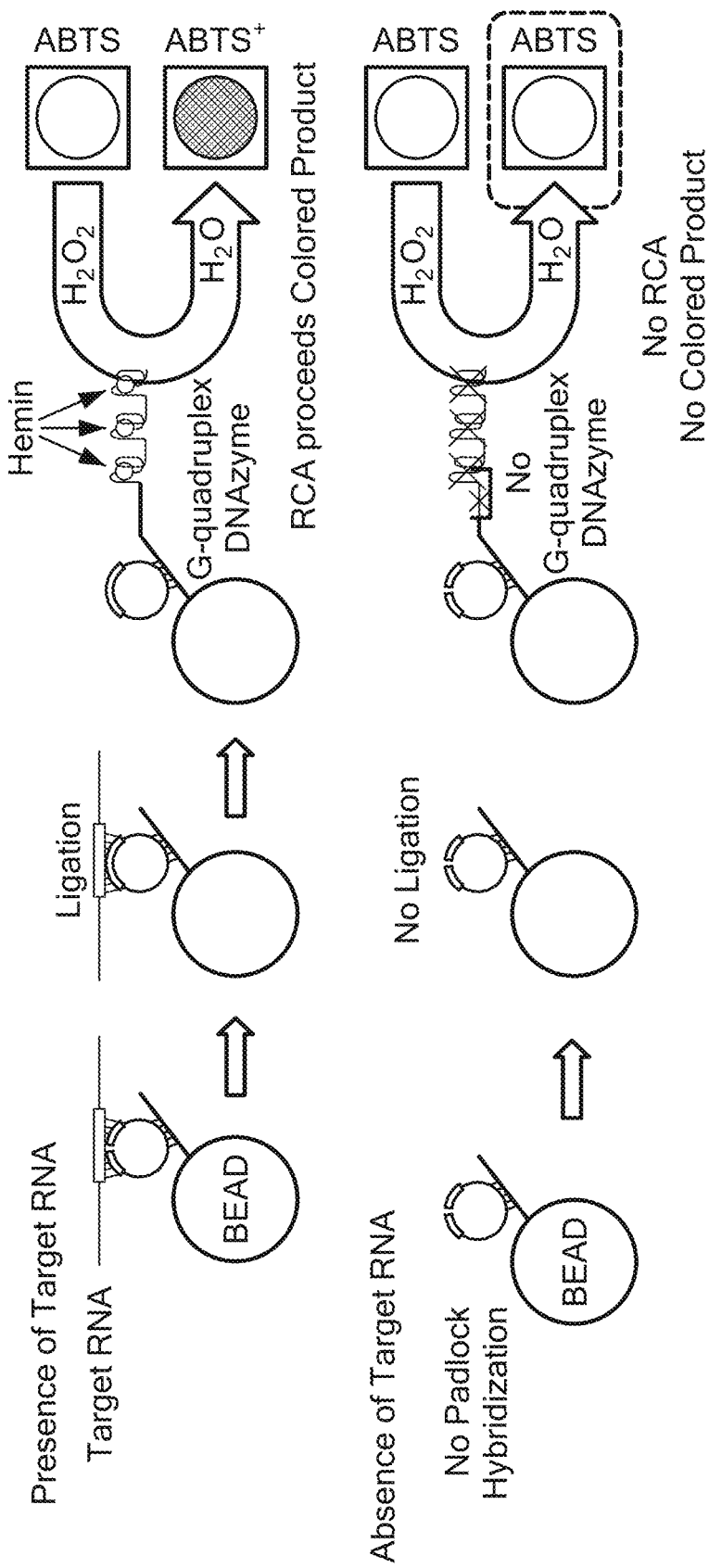
FIG. 1A shows a schematic diagram of a process of detecting the presence or absence of a target RNA molecule using rolling circle amplification (RCA) in which the RCA initiation primer is attached to a bead. The padlock probe contains a detection sequence that encodes a G-quadruplex DNAzyme that catalyzes the formation of a colored product in the presence of the target RNA molecule.

The present technology provides rapid, multiplex detection of nucleic acid molecules from a sample at high sensitivity and using a fully automated system. The technology uses rolling circle amplification (RCA) methodology to detect RNA or DNA by amplifying a detection signal to achieve specific detection at the level of picomoles to attomoles of a target nucleic acid. The technology can be implemented in a variety of different formats, including MEMS or microfluidic platforms and point-of-care devices such as lateral flow paper-based tests. The technology also can be carried out in different formats using primers conjugated to microbeads or other solid supports, which can be differently labeled for use in multiplex assays. The technology is particularly suited for use as a screening assay to detect and differentiate between two or more different viruses or other pathogens in a sample, such as distinguishing between COVID-19 and other respiratory viral infections such as influenza, or identifying which of several possible strains of a virus is present in a patient sample.

The methods of the present technology utilize RCA for detection of nucleic acids (RNA or DNA) in a sample. The sensing mechanism for RCA is the use of the target nucleic acid as a ligation initiator for formation of a circular DNA from a linear DNA probe known as a padlock probe. In the presence of a target sequence of the target nucleic acid molecule, such as a specific viral RNA, in the sample allows the ligation of the circular DNA, which then becomes available to serve as a template for a continuous RCA reaction. The absence of the target RNA prevents the ligation of the probe to form a circular DNA, on whose presence the whole RCA reaction depends. Once the ligated circular DNA forms, the RCA reaction will, with the help of a DNA polymerase, extend an RCA initiation primer, resulting in the formation of multiple copies of a detection sequence that was included as part of the padlock probe. The amplified detection sequence, or more precisely its reverse complement, can then be used to create a detectable signal which indicates the presence of the target sequence in the sample.

The present technology makes use of several strategies to enhance the sensitivity of detection of a target nucleic acid molecule by RCA as well as to render the detection simple to carry out and automatable for use in high throughput screening of samples, such as during a pandemic. Since RCA can be carried out isothermally, unlike polymerase chain reaction (PCR), the methods of the present technology can be used for point of care testing. While a typical RCA reaction can produce several copies of a detection sequence, for more sensitive detection the present methods can use multiple padlock probes binding to different target sequences within a single target nucleic acid molecule, such as a viral genome. This approach takes advantage of more favorable reaction kinetics when using multiple padlock probes binding to each target molecule. The present methods also can produce still more copies of a detection sequence by employing circle-to-circle RCA, in which the linear single-stranded DNA product of a first cycle of RCA is separated into several circle-forming padlock sequences, each of which can be used to extend an RCA primer in second and subsequent rounds of RCA, leading to extensive amplification of the detection signal. Another strategy of the present technology is the use of a solid support conjugated to the primer for an RCA reaction, to allow the manipulation of RCA products and to enable exchange of solutions and application of different enzymes of the RCA process. These strategies combine to yield a rapid, easily executable and scalable diagnostic assay for detection and optionally for quantification of any target nucleic acid molecule from a virus, prokaryotic cell, or eukaryotic cell.

The present technology has several advantages over conventional RT-PCR technology. Analysis time is much shorter at 1-4 hours instead of 5-6 hours for RT-PCR. The analysis can be carried out using a fully automated system without the need for highly trained labor. In some embodiments, the analysis can be performed using lightweight, portable devices that can be adapted for field applications. Multiplex analysis can be performed to differentiate between different viral infections in a patient that have similar clinical symptoms, for rapid determination of which type of infection the patient has. The small scale of embodiments such as microfluidics offer reduced consumption of analytical reagents including molecular detection probes, thus lowering the cost per assay. Finally, the optimum sensitivity is greater, essentially at the level of a single nucleic acid molecule added to the assay from a sample.

Any material can be used as a sample for analysis of a nucleic acid in the material using the present technology. However, many types of materials will require some form of extraction, purification, or other forms of preliminary processing such as filtration, centrifugation, deactivation of enzymes such as nucleases present in the sample, detergent treatment, homogenization, dilution, concentration, or the like, which are well known to practitioners of nucleic acid analysis. Commercially available kits and reagents for RNA or DNA extraction and sample preparation can be used. Liquid samples are preferred, and include any bodily fluid such as blood, serum, plasma, saliva, mucus, and urine.

Carrying out an RCA reaction for detection of a target nucleic acid molecule includes three basic steps of ligation, elongation, and detection. Ligation requires hybridization of a special template molecule, also referred to as a padlock probe, to the target molecule, and ligation of the ends of the padlock probe to form a circular nucleic acid molecule, which serves as template for the RCA reaction. Hybridization can be carried out under stringent conditions that allow hybridization to occur only between sequences having full complementarity, or nearly full complementarity, such as at least 95%, at least 97%, at least 98%, at least 99%, or 100% complementarity. While the padlock probe can be any type of nucleic acid molecule, such as DNA, RNA, or a synthetic nucleic acid, DNA is preferred due to the availability of enzymes for ligating and polymerizing DNA from a target nucleic acid molecule, which can be a naturally occurring RNA or DNA molecule. Suitable enzymes for ligation include T4 DNA ligase and other template-requiring ligases, such as template-requiring DNA ligases. The use of template-free ligases such as CircLigase™ should be avoided, as their use would render the RCA reaction independent of the presence of the target nucleic acid molecule.

In addition to the circular template, or circularized padlock probe, formed by ligation, a primer is required to perform an RCA elongation reaction. Such a primer, referred to herein as an "RCA initiation primer", hybridizes with a "primer binding sequence" which is contained in the padlock probe. The primer is thus a short single-stranded nucleic acid molecule (e.g., an RNA or DNA or synthetic nucleic acid) that optionally can be attached (e.g., covalently conjugated) to a solid support. The primer includes a "padlock binding sequence" which is complementary to the primer binding sequence. Once the circularized padlock probe is hybridized to the RCA initiation primer, elongation (or amplification) of the primer can be carried out using a nucleic acid polymerase, such as Phi29, Bst, or Vent exo- DNA polymerase for DNA extension or T7 RNA polymerase for RNA extension. Preferably the polymerase has high processivity and strand displacement. The resulting product is a single-stranded nucleic acid (e.g., DNA or RNA) that contains multiple copies of the padlock probe sequence, including its detection sequence. The ligase and polymerase reactions of RCA can be carried out at a constant temperature, such as ambient temperature (room temperature), such as about 15 to 30° C., or at 37° C., or at an elevated temperature such as about 40, 45, or 50° C.; higher temperatures such as 60-80° C. can be used if the required enzymes are sufficiently stable.

Detection of the amplified detection sequence can be by any known method, but two methods are preferred: fluorescence detection and generation of a visible colored product. Fluorescence detection can be accomplished by integrating fluorophore-conjugated dNTPs into an oligonucleotide product generated from the detection sequence, or by hybridization of the detection sequence to a fluorescently-labeled molecular beacon or other detection probe.

Figure 1B:
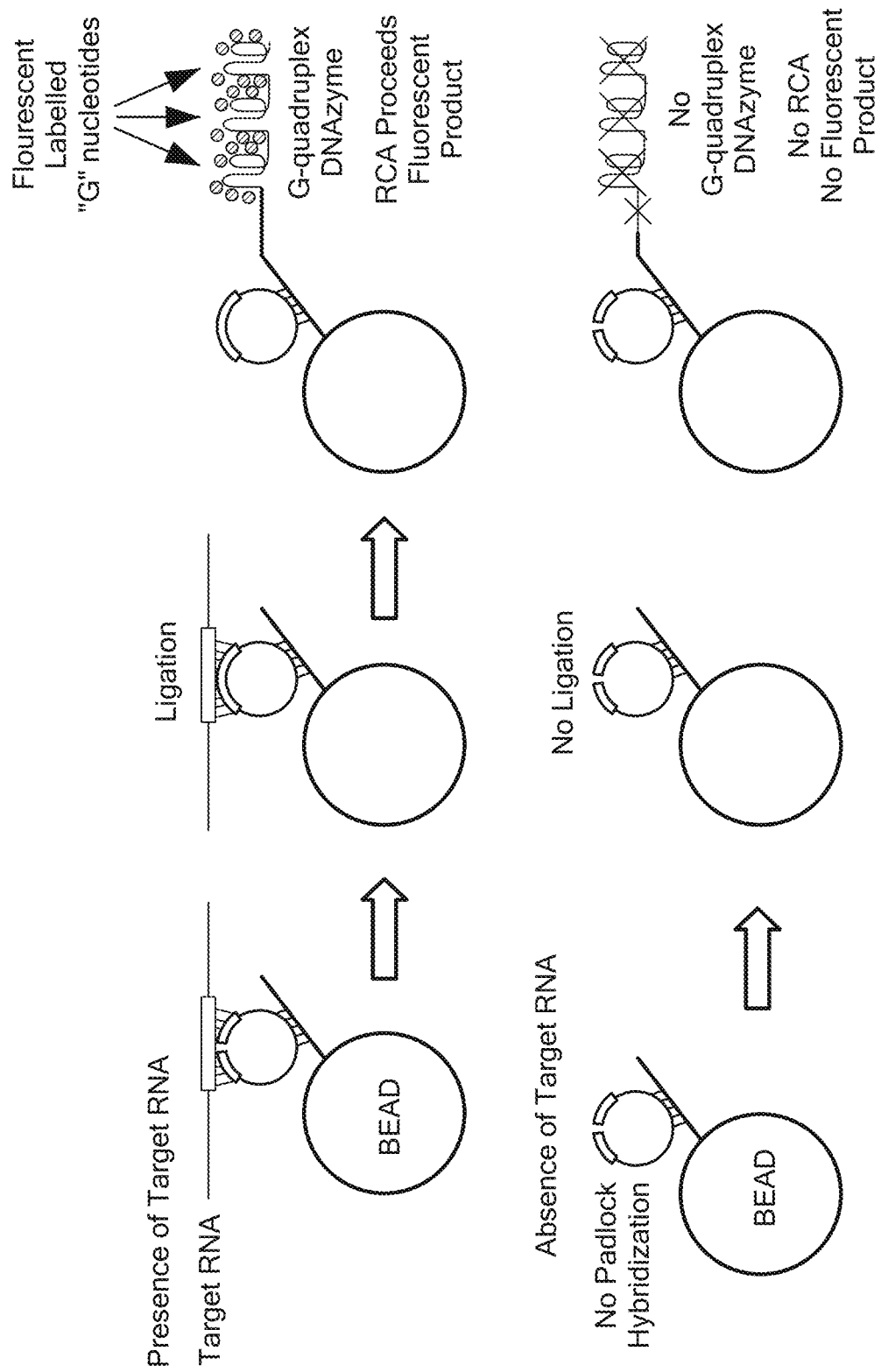
FIG. 1B shows a similar process in which the padlock probe contains a detection sequence enriched in guanine nucleotides, allowing enriched incorporation of fluorescently labeled guanine nucleotides from the extended RCA primer for detection of the presence of the target RNA molecule.

In a preferred embodiment, the RCA reaction is carried out using an RCA initiation primer covalently attached to a microbead or other form of solid support. For example, microbeads of any material typically used in nucleic acid analysis, such as polyethylene, polypropylene, polystyrene, polyethylene terephthalate, nylon, or poly(methyl methacrylate), and having a diameter of about 5, 10, 15, 20, 30, 40, 50, 60, 70, 80, 90 or 100 µm can be used. The beads can be obtained commercially prepared with attached streptavidin for ready conjugation with biotinylated nucleic acid probes. The beads can optionally be magnetic to aid their retrieval and manipulation. The RCA primer can be conjugated to the microbeads at a level of, for example, about 0.1, 0.2, 0.3, 0.5, 1, 2, 5, or 10 µg of primer DNA per 1 mg of microbeads; the amount can be readily estimated and optimized by a person of skill in the field. The microbead may be in turn attached to a surface of a device or free flowing within a microfluidic device, arranged in a microarray of microbeads, or used in suspension with standard pipetting and centrifugation, filtration, or magnetic retrieval techniques. FIGS. 1A and 1B illustrate how an RCA reaction can be carried out in this configuration. First, the target nucleic acid is hybridized to a DNA padlock probe, which is ligated using a DNA ligase, forming a single-stranded circular product bound to the RCA primer. A DNA polymerase is then used to elongate the primer to form a single-stranded DNA product which remains conjugated to the microbead or other solid support. The single-stranded DNA product contains several copies of the circular DNA, including a detection sequence. The detection sequence can form a G-quadruplex structure that coordinates with added hemin to form a DNAzyme capable of carrying out a peroxidase-like reaction, in which a substrate, such as ABTS (2,2'-azino-bis(3-ethylbenzothiazoline-6-sulfonic acid), can be oxidized with $H_2O_2$ to form a colored product. The assay can be configured to yield only a positive or negative result, with accumulation of the colored product (dark green in case of ABTS), visible to the unaided human eye, indicating the presence of the target sequence and no accumulation of the colored product indicating the absence of the target sequence; however, the assay also can be configured to provide a quantitative determination of the amount of colored product read by a spectrophotometer and compared to a standard curve for quantification. An alternative method of visualizing copies of a detection sequence is by fluorescence. The padlock probe contains a detection sequence which is enriched in, or is entirely limited to, any desired single nucleotide (i.e., A, T, C, or G); this allows the detection sequence to be labeled with a single type of fluorescent using a DNA polymerase, for example. FIG. 10 shows how the fluorescence assay can be multiplexed. Padlock probes having different target binding sequences as well as different detection sequences can be labeled with different fluorescence emissions. The number of simultaneously detectable targets can be increased by the use of combinatorial labeling, in which different fluorescent microbeads are conjugated to primer sequences that specifically bind a selected padlock probe, whose detection sequence is detectable with a fluorescently labeled base to provide a unique combination of fluorescence emissions.

An RCA-based detection or quantification assay of the present technology can be performed using a variety of different formats or devices. The assay can be performed in solution with pipetting of reagents and purification of products using conventional biochemical techniques. However, in preferred embodiments the assay is performed either in automated fashion for high throughput or using a portable and preferably single-use point-of-care device. In any format, the assay can be multiplexed for the detection or quantification of two or more target nucleic acid molecules simultaneously, or used in non-multiplexed fashion for the detection or quantification of a single target nucleic acid molecule. Multiplexing is preferred because it can provide not only identification of a target nucleic acid, but also can provide confirmatory information such as absence of other target nucleic acids or identification of which strain of a pathogen, or which one of several pathogens is present among a group of pathogens producing similar disease symptoms, such as a group of viruses causing respiratory infections.

Figure 2A:
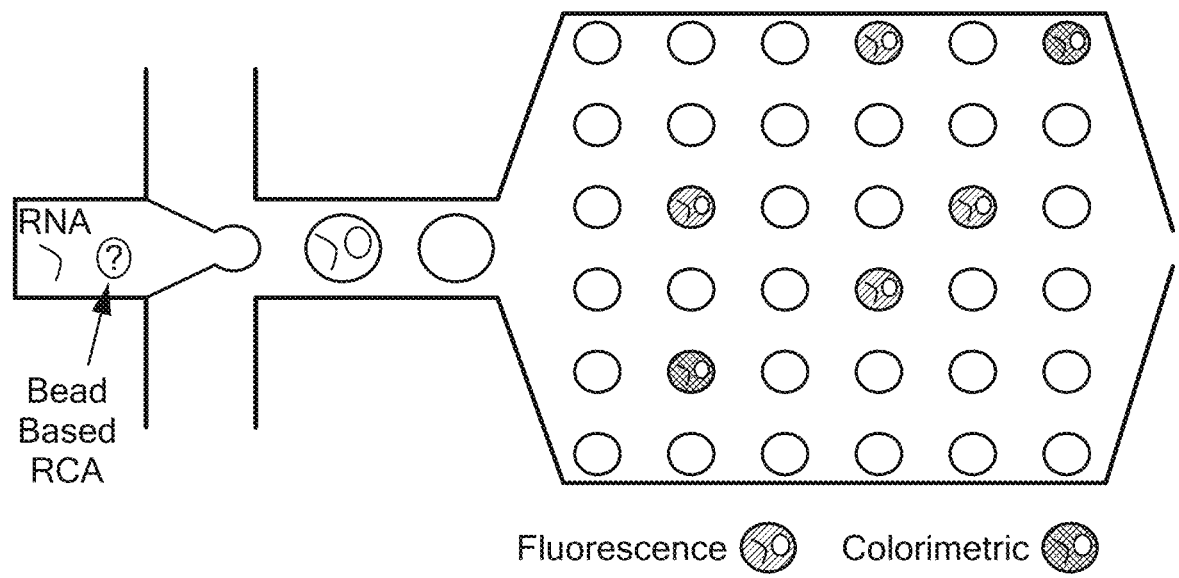
FIGS. 2A-2D show embodiments of the use of a microfluidic device for detection of the presence, absence, or amount of a target nucleic acid molecule.
Figure 2B:
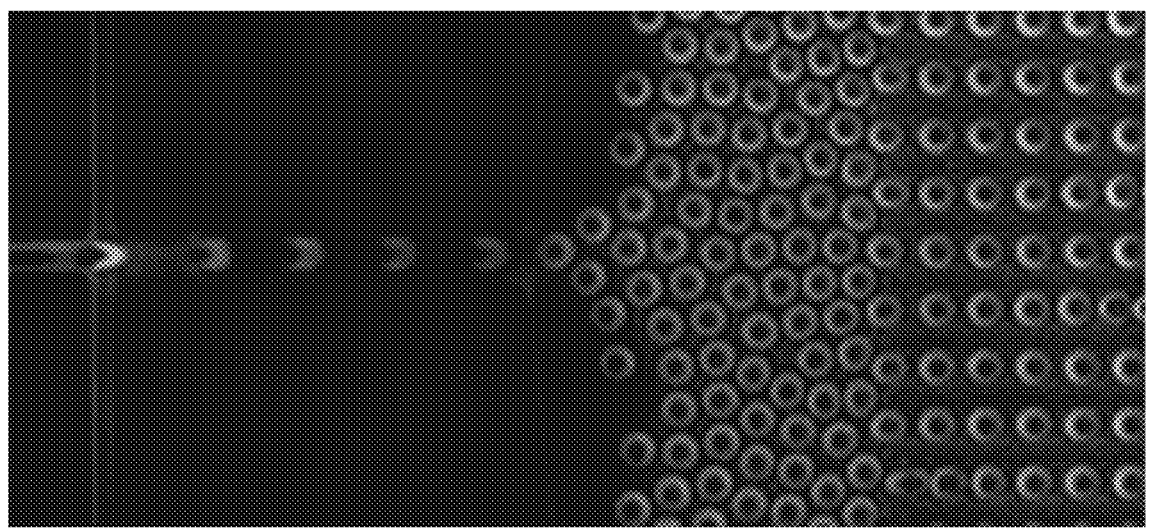

A preferred format for detecting the presence or absence, and/or quantifying, of a target nucleic acid molecule is the use of a microfluidic device or chip. Microfluidic devices and methodology are available that offer high throughput, rapid, sensitive, and optionally multiplexed performance of RCA using either aqueous microdroplets in oil or primers bound to microbeads or other solid support surfaces within the microfluidic device. FIG. 2A shows a schematic representation of a microfluidic device capable of forming aqueous microdroplets at a junction between microfluidic channels containing an aqueous solution and an oil. The aqueous solution can include target nucleic acids (e.g., RNA) as well as microbeads to which are conjugated RCA primer molecules. During droplet formation, target molecules become entrapped together with the microbeads and other needed reagents (e.g., buffer, enzymes, dNTPs, etc.) in a series of microdroplets which are then loaded into an array of microchambers or docking stations shown at the right, where the microdroplets can be observed using an imaging device (e.g., a fluorescence microscope, spectrophotometer, or other optical device). As shown in FIG. 2A, such microfluidic devices can use either fluorescent or colorimetric detection, or even both combined in a single multiplex assay that employs different detectors for different targets (e.g., both fluorescence and colorimetry). FIG. 2B shows an actual microfluidic device in which microdroplets are being formed and loaded into a microarray chamber. Further details of microfluidic devices capable of forming and analyzing aqueous microdroplets can be found in US2018/0203005A1, which is hereby incorporated by reference.

Figure 2C:
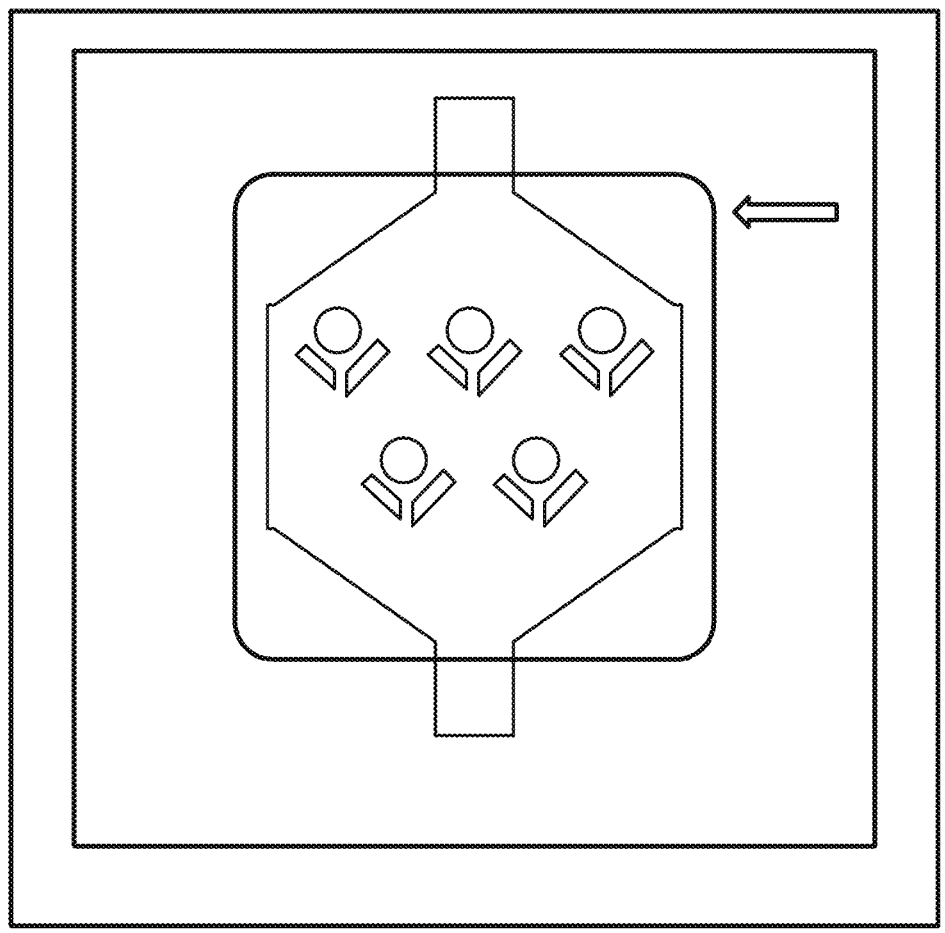
Figure 2D:
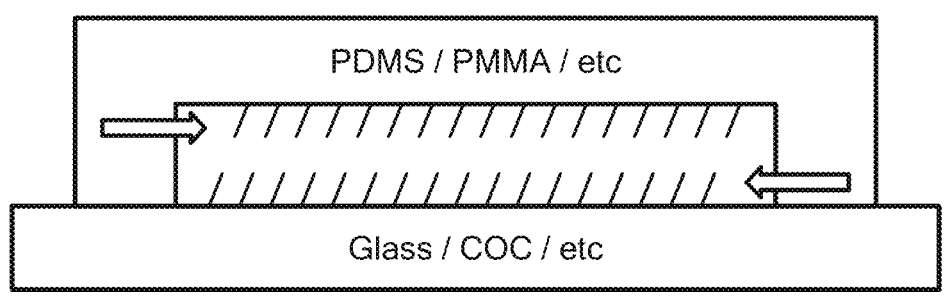

FIG. 2C shows a different embodiment in which microbeads suspended in an aqueous solution have been loaded into a docking array in a microfluidic device. FIG. 2C depicts the array chamber with inlet at top and outlet at bottom. The microbead suspension flows through the chamber from top to bottom, and microbeads (black circles) become trapped at the V-shaped docking structures. The array chamber has an optical window (square indicated with arrow) above the beads, which permits visual and/or microscopic observation of color or fluorescence development at the microbeads over time. The array chamber can be perfused with enzymes and other reagents for carrying out an RCA reaction, while the products remain trapped on the microbeads through their conjugated primers. FIG. 2D shows a schematic of a cross-section of a microfluidic channel or chamber of a microfluidic device in which one or more internal surfaces of the device are conjugated to RCA primers. Like the microbeads, the conjugated patches or other structures can be arranged into desired patterns useful for indicating results of positive or negative detection. Known chemistries are available for conjugating oligonucleotides (e.g., single-stranded DNA) to surfaces having different compositions, such as surfaces including poly(dimethylsiloxane) (PDMS) or poly(methyl methacrylate) (PMMA), often used to form the channel-containing upper portion of a microfluidic device, or glass or cyclic olefin copolymer (COC), often used to form the base of a microfluidic device, including channels and reagent chambers.

Performing RCA-based detection of nucleic acids using a microfluidic device has the advantages of high throughput and high sensitivity. The microdroplet platform can handle high throughput analysis of one million samples for short-term analysis and 100000 samples for longer term analysis. Different countable numbers of labeled droplets in the device can indirectly represent a certain concentration of target molecules in the sample. For example, if 10 droplets contain the measurable detection signal, either by fluorescence or colorimetry, the sample RNA concentration can be related back to a known concentration, such as 10 droplets being equivalent to 1 pM concentration and 30 droplets is equivalent with 1 μM concentration. This can speed analysis where exact quantification is not required, and the large number of microdroplets analyzed simultaneously can still allow for simultaneous analysis of many samples, such as many patient samples.

A preferred embodiment for implementing the present technology in a point-of-care device uses a paper-fluidic format. Such devices can be useful for field virus detection, rapid screening, or repeated testing of large populations at low cost and with fast feedback for the tested individual, to promote contact tracing or to screen individuals at crowded facilities such as airports and large meeting, concert, or sports venues. The paper can have a specific detection area embedded with RCA primers conjugated to beads or to the paper or other support material. RCA reaction products bound to the beads or detection area surface can be detected using either fluorescence or colorimetric measurements. The output can be a simple positive (presence) or negative (absence) result, or a quantitative or semi-quantitative result by comparison to a chart of color or fluorescence intensity, or by using an optical reader device. The paper fluidics platform does not require heavy or expensive thermocycling equipment as is required for an RT-PCR assay for virus detection. The device can be configured to include the required reagents, with the only requirement in the field being the sample or an RNA or DNA extract thereof.

Figure 3A:
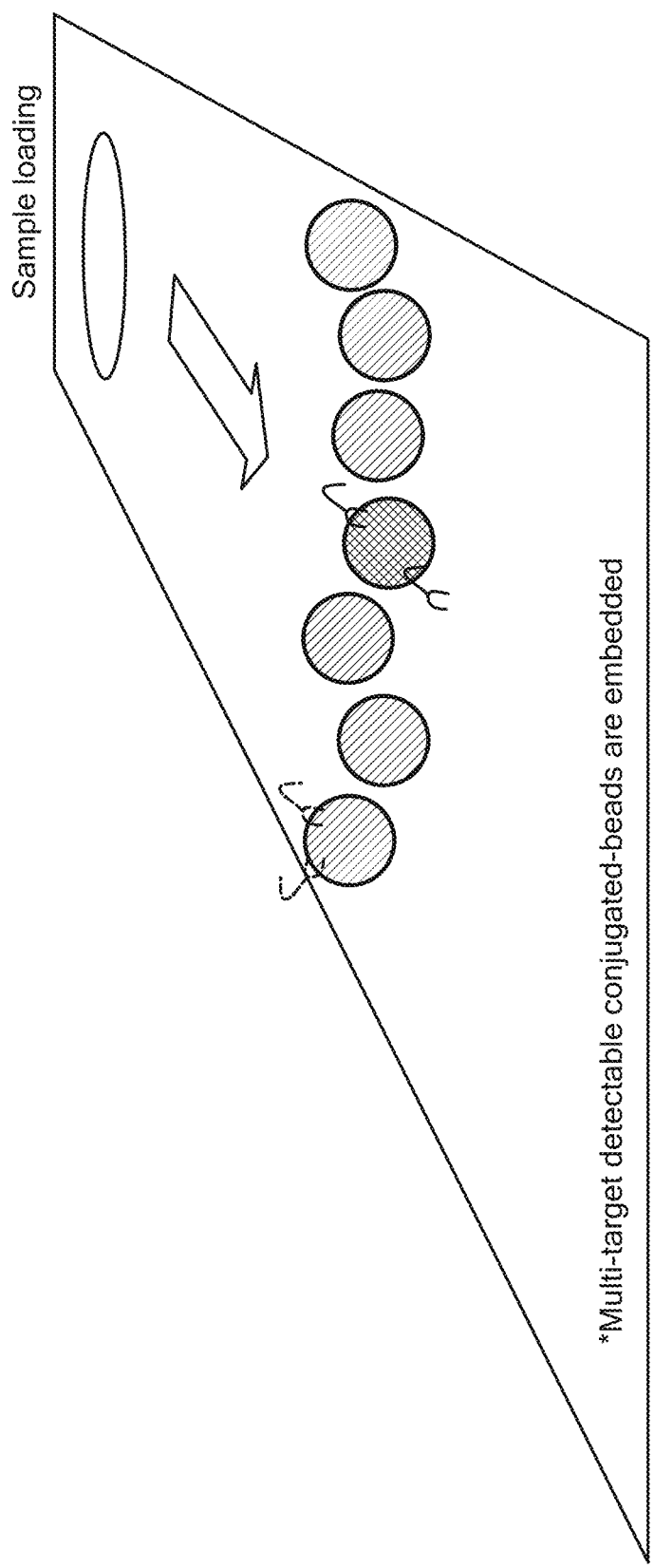
FIGS. 3A-3C are schematic representations of paper fluidic embodiments of a process for detecting presence or absence of a target nucleic acid molecule using RCA.
Figure 3B:
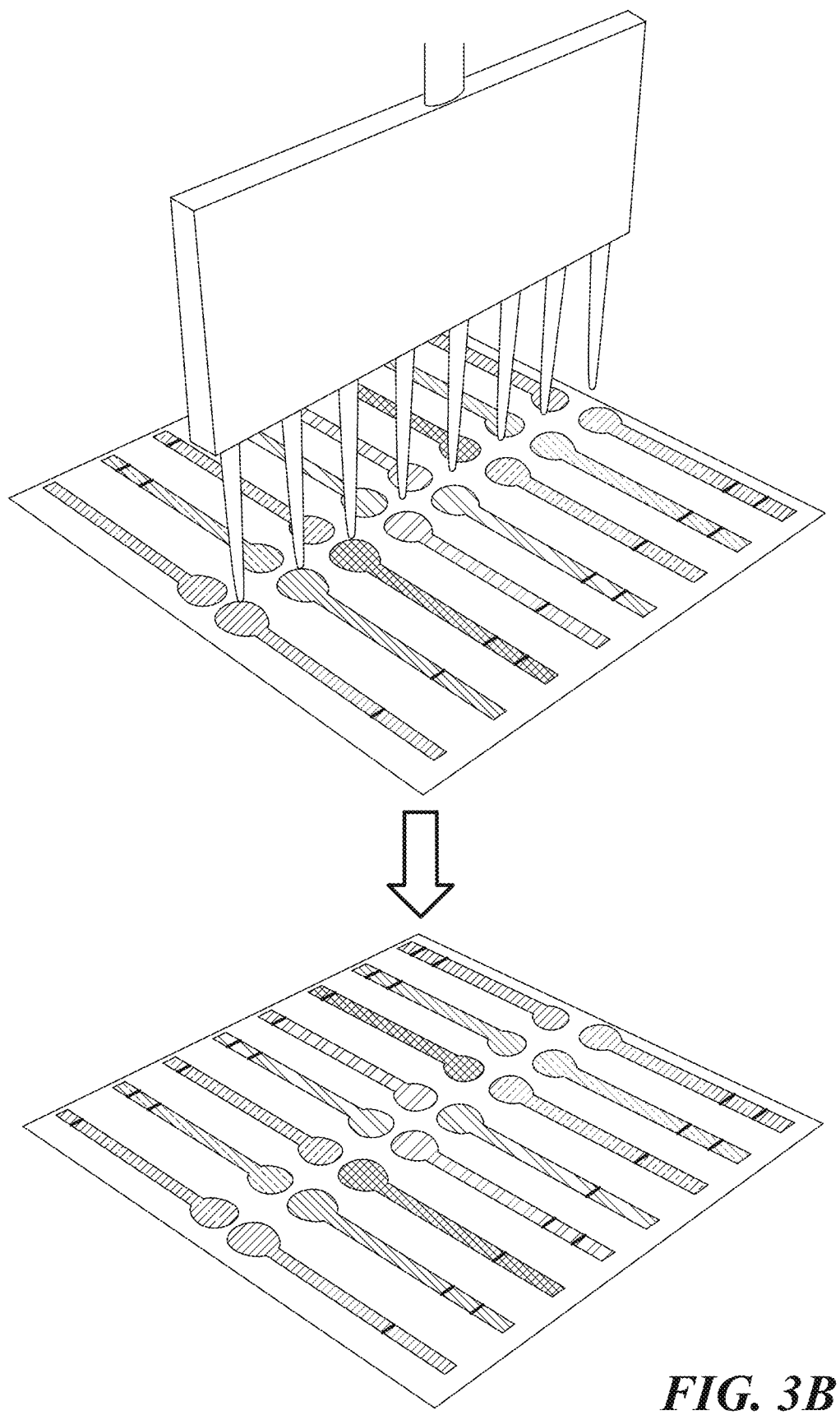
Figure 3C:
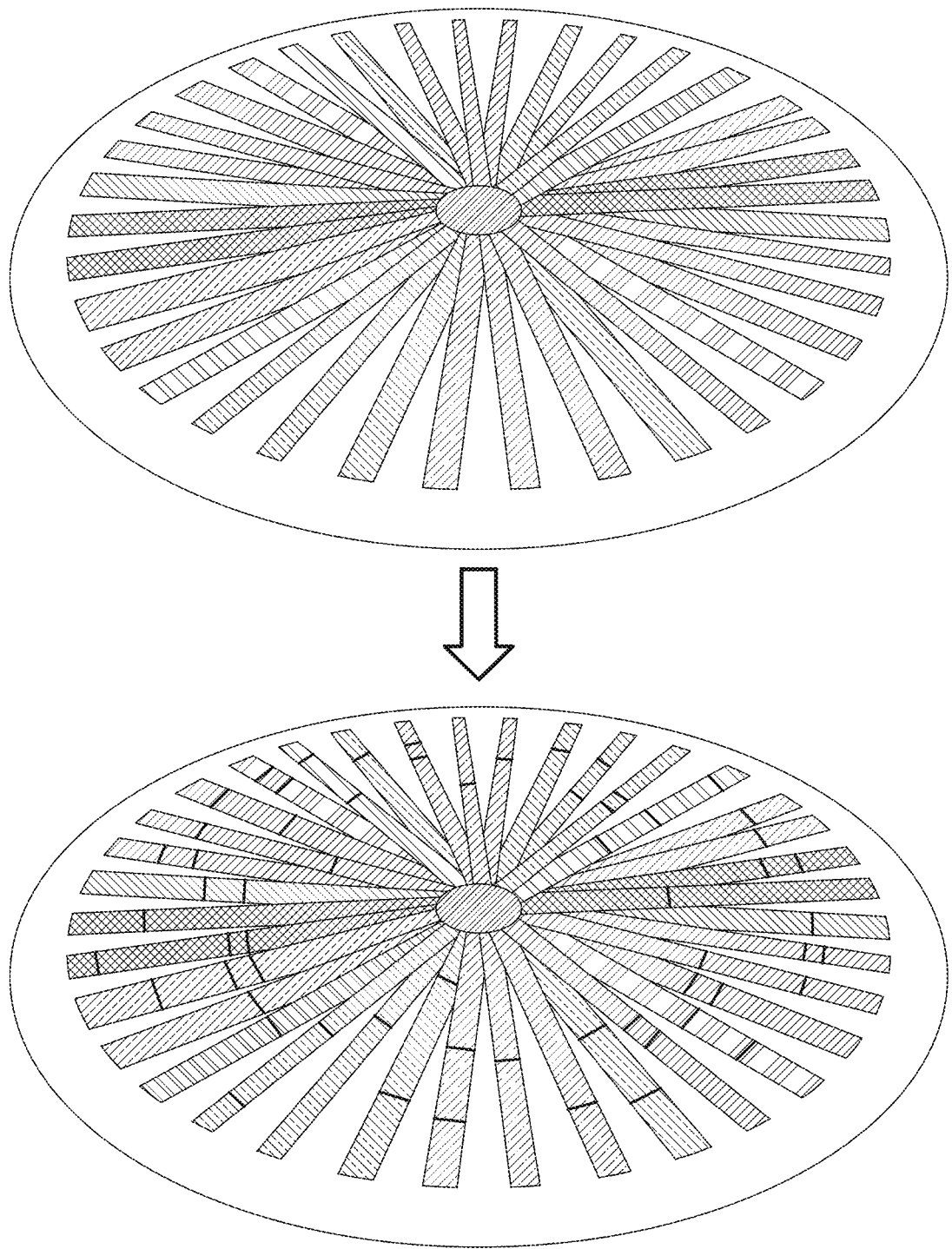

FIG. 3A shows a general illustration of a multiplex version of a paperfluidic POC device having two different types of microbeads, each conjugated to a different RCA primer and producing a differently colored product, embedded at a selected position in a paper solvent track. A reaction mix including the sample suspected of containing a target nucleic acid molecule, one or more padlock probes, required buffer constituents, and optionally also including a DNA ligase, are added to the sample loading zone. Buffer is flowed along the paper to develop the reaction, leading to hybridization and formation of circularized probes at the microbeads when the target nucleic acid molecule is present in the sample. Subsequent addition of a polymerase reaction mix (DNA polymerase and substrates (e.g., dNTP mix containing one type of fluorescently labeled base (i.e., A, G, C, or T) at the sample loading position or another loading position results in transport of the reagents to the microbeads, where the extension reaction and color development take place. Concentration of fluorescent bases at the respective microbeads provides a visible or optically quantifiable readout under suitable illumination. FIGS. 3B and 3C show two further designs suitable for multiplex analysis, in which multiple samples or a sample plus different types of probes or other reagents, are applied to multiple sample placement areas connected to different analysis tracks (FIG. 3B) or a single sample placement area connected with radially distributed different analysis tracks (FIG. 3C); the different analysis tracks can have different embedded microbeads with different primers designed to capture different sets of probes related to detection of different targets. As a variation of these embodiments, RCA primers can be conjugated directly to the substrate at selected positions instead of using microbeads. The substrate can be a different material than paper, such as a polymer material.

FIGS. 4A and 4B illustrate the design of three padlock probes for specific detection of SARS-CoV-2. Each of the probes is a single-stranded DNA molecule containing a target binding sequence that is split in the middle, with one half located at the 3' end of the probe and the other half located at the 5' end, and oriented such that both halves can hybridize to the target sequence leaving only a gap between the hybridized 3' and 5' ends which can be closed by a DNA ligase. The central probe sequence between the two terminal target binding sequences includes a detection sequence and a primer binding sequence. Optionally, if the probe is used for C2C RCA, the central probe sequence also includes a restriction enzyme cleavage site for use in separating copies of the probe in the extended RCA product. In the embodiment shown in FIGS. 4A and 4B, the target binding sequences of the three probes are directed to N1, N2, and N3 regions of the N gene transcript. These three probes can be used as a set for detection or quantification of SARS-CoV-2 RNA in a sample. The three different probes can all possess the same primer binding sequence, in which case each probe will contribute to generating a common detection signal and result. The use of all three probes together increases the sensitivity and accuracy of the analysis by detecting different fragments of the N gene transcript and reducing false positive results.

Figures 5A, 5B:
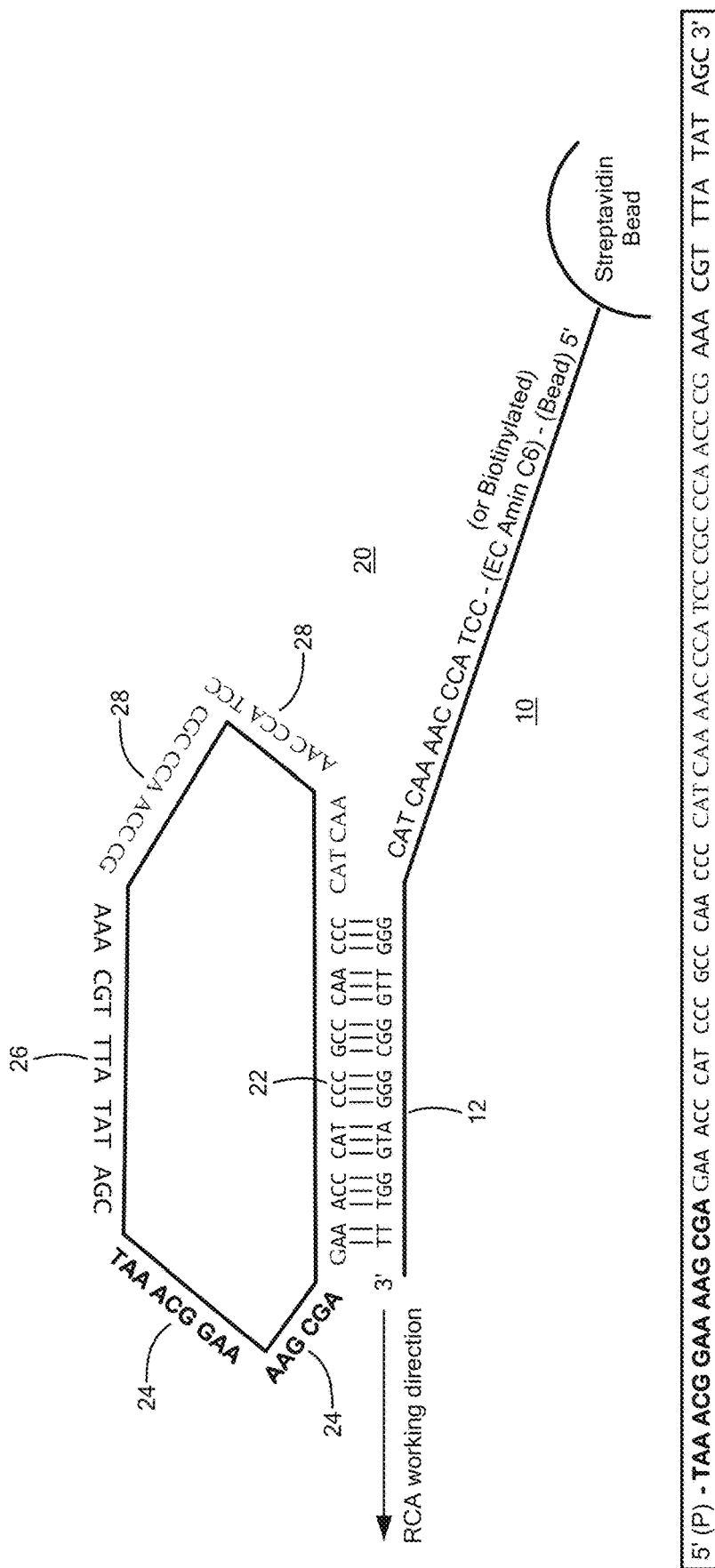
FIG. 5A shows the sequence of an unligated padlock probe (lower part of figure, SEQ ID NO:15) suitable for binding to a region of the N gene of SARS-CoV-2, and how the ligated padlock probe (circular single-stranded DNA) hybridizes to a corresponding RCA initiation primer (SEQ ID NO:14).
FIG. 5B shows two additional unligated padlock probe sequences suitable for binding to other regions of the N gene of SARS-CoV-2. The sequences are SEQ ID NO:16 (N2 probe) and SEQ ID NO:17 (N3 probe).

FIG. 5A illustrates the detailed interaction of an embodiment of a circularized padlock probe and an RCA initiation primer. Primer 10 is attached to a microbead through interaction of the biotinylated 5' end of the primer and streptavidin attached to the bead. After a short spacer segment, the 3' terminus includes padlock binding sequence 12 that is complementary to primer binding sequence 22 on circularized padlock probe 20. Once the probe is hybridized to the primer, a DNA polymerase can extend the primer from its 3' end. Other components of the circularized probe are target binding sequences 24 (originating from 5' end, and 26 (originating from 3' end) and detection sequence 28. The linearized (pre-ligation) form of the probe is shown at the bottom of FIG. 5A. FIG. 5B shows two additional linearized probe sequences (having the same target binding sequences at the probes depicted in FIG. 4B) which, together with the probe of FIG. 5A, form a set for detection of SARS-CoV-2 by colorimetric detection. The set shares a common primer binding sequence as well as a common detection sequence, which is capable of forming a G-quadruplex for colorimetric detection.

Figures 6A, 6B:
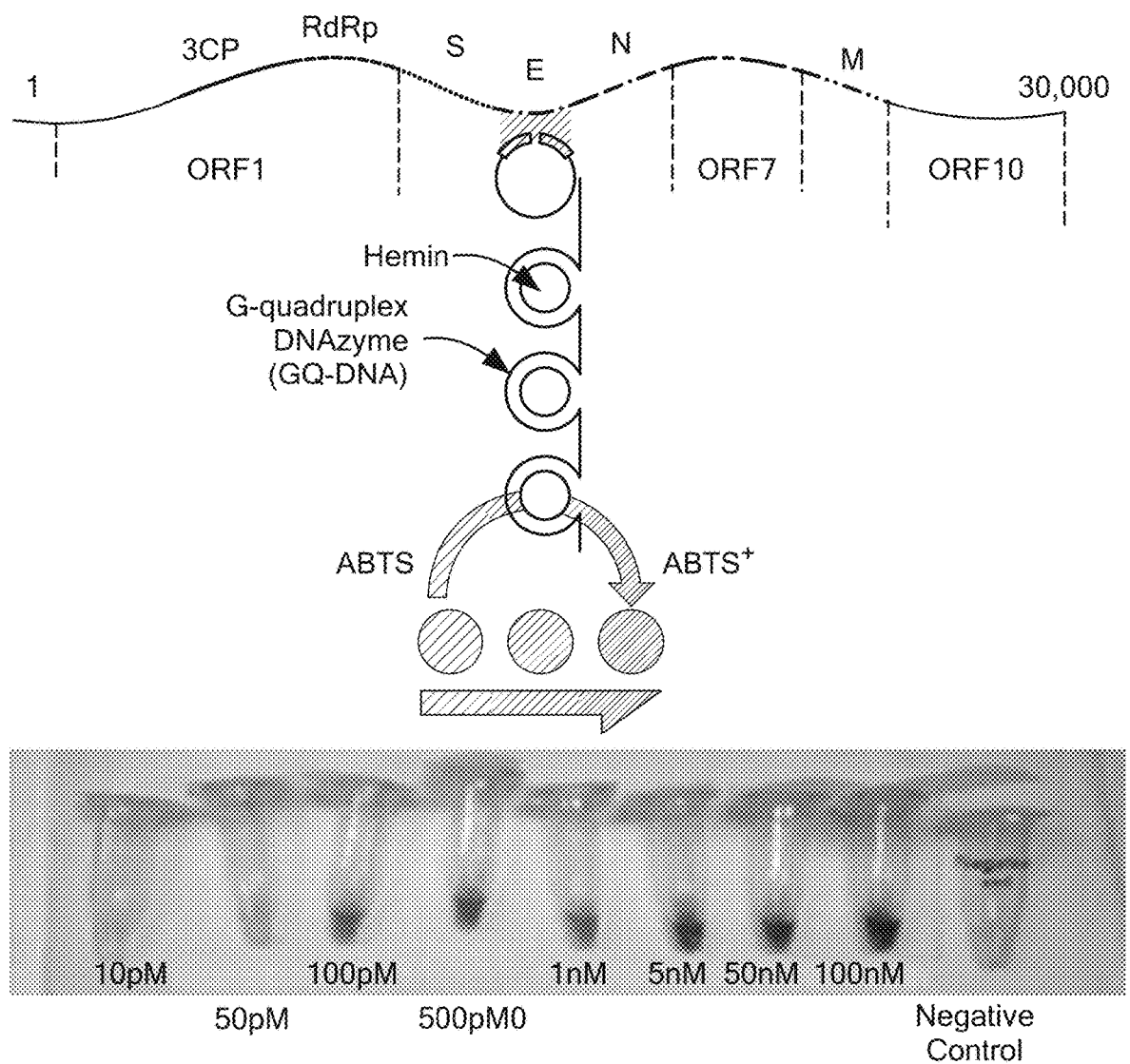
FIG. 6A shows an embodiment of a detection sequence (SEQ ID NO:18) of a padlock probe.
FIG. 6B shows a schematic illustration of colorimetric detection of the E gene of SARS-CoV-2 using RCA to produce multiple copies of a detection sequence that encodes a G-quadruplex DNAzyme which can be used to produce a colored product (ABTS) by a peroxidase-like reaction. The photo at the bottom of the figure shows centrifuge tubes containing the colored ABTS product as a function of concentration of a target RNA (N gene from SARS-CoV-2).

FIG. 6A shows a DNAzyme forming detection sequence. FIG. 6B shows diagrammatically how this sequence leads to formation of a colored ABTS product in the presence of a target sequence found in the E gene segment of a SARS-CoV-2 RNA transcript. Amplification of the detection sequence leads to the formation of multiple copies of the detection sequence, each of which is capable of forming a DNAzyme (GQ-DNA. The DNAzymes form coordinate complexes with hemin which, in the presence of $H_2O_2$, form a colored product in proportion to the amount of target RNA present in a sample. The series of microcentrifuge tubes at the bottom of FIG. 6B shows color development as ABTS generated using 10 pM through 100 nM target RNA.

The sensitivity of the RCA-based detection of target nucleic acids according to the present technology, which is the smallest concentration of target nucleic acid detectable in a sample, is determined in particular by the amount of detectable signal produced per molecule of target added to the assay. This, in turn, is a function of the amount of amplified detection sequence produced in the RCA process. Thus, the present inventors have discovered that a key way of increasing sensitivity is to increase the number of padlock probes utilized per target nucleic acid molecule. Particularly for long nucleic acids, such as viral genomes, bacterial genomes, or polycistronic mRNA transcripts, a large number of distinct target sequences can be detected per molecule, and a unique padlock probe can be constructed for each such target sequence. FIG. 7A shows further that the number of copies of the detection sequence obtained for a given target is equal to the number of copies of the target molecule added from the sample (determined by the concentration of target molecules in the sample) times the number of copies of a single padlock probe directed to the target sequence (determined by the concentration of the padlock probe used in the assay). That is, the ligation reaction that initiates the RCA amplification process is a second order reaction. However, as shown in FIG. 7B, if the number of padlocks directed against each target molecule is increased, then the sensitivity is increased by a multiplication factor equal to the number of padlock probes. For example, if the goal is to detect SARS-CoV-2 RNA in a sample, then the sensitivity is multiplied by the number of distinct padlock probes utilized, where each padlock probe is directed to a distinct target sequence within the SARS-CoV-2 RNA molecule. A polycistronic RNA molecule like the SARS-CoV-2 mRNA presents many targets, and numerous target sequences can be selected, several from each gene product. Using this approach, at least 500 targets can be generated from SARS-CoV-2 RNA, greatly increasing the sensitivity of detection.

This principle has been used in the current technology to extend sensitivity down to the attomolar range for target molecules that can support, for example at least 100, at least 200, or at least 500 target sequences. Thus, while the RCA process can be carried out using a single type of padlock probe detecting a single target sequence within the target nucleic acid molecule, sensitivity can be greatly increased by increasing the number of distinct padlock probes to at least 2, at least 3, at least 5, at least 10, at least 20, at least 30, at least 50, at least 100, at least 200, at least 300, at least 500, or even at least 1000 padlock probes per target molecule. The number of possible target sequences available will depend on the length of the target molecule and the length of the target sequence selected for each probe. Note that this approach is not considered "multiplexing" in the present technology because detection is of a single target nucleic acid molecule.

The target sequence used in each unique padlock probes is preferably from about 20 to about 40 consecutive nucleotides selected from the target molecule, preferably about 25 to about 35 consecutive nucleotides, more preferably about 30 consecutive nucleotides. Target sequences can usually be selected at random from a target molecule nucleotide sequence, although various algorithms are available to determine whether certain sequences might be unsuitable as target sequences and should be avoided. In different embodiments, the target sequences do no overlap, or may overlap by about 5, about 10, about 15, or even about 20 nucleotides.

Figure 8B:
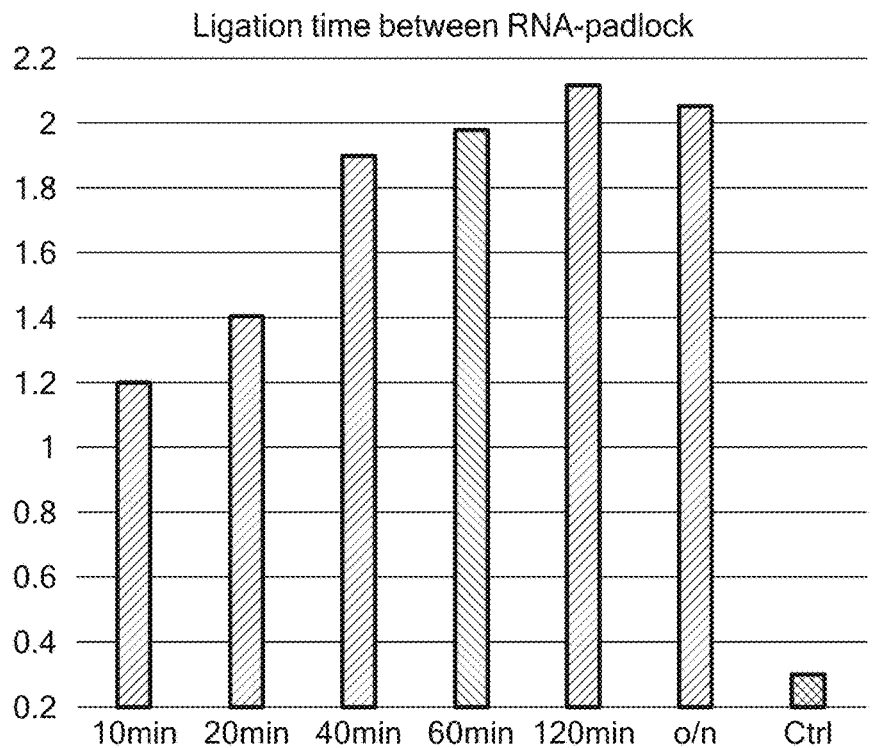
FIG. 8B shows the result of a similar experiment to optimize ligation time between a target RNA molecule and a padlock probe. The graph shows the concentration (µM) of ligated DNA as a function of time; the same padlock probe was used as in FIG. 8A, directed to a target sequence of 30 nucleotide bases.
Figure 8C:
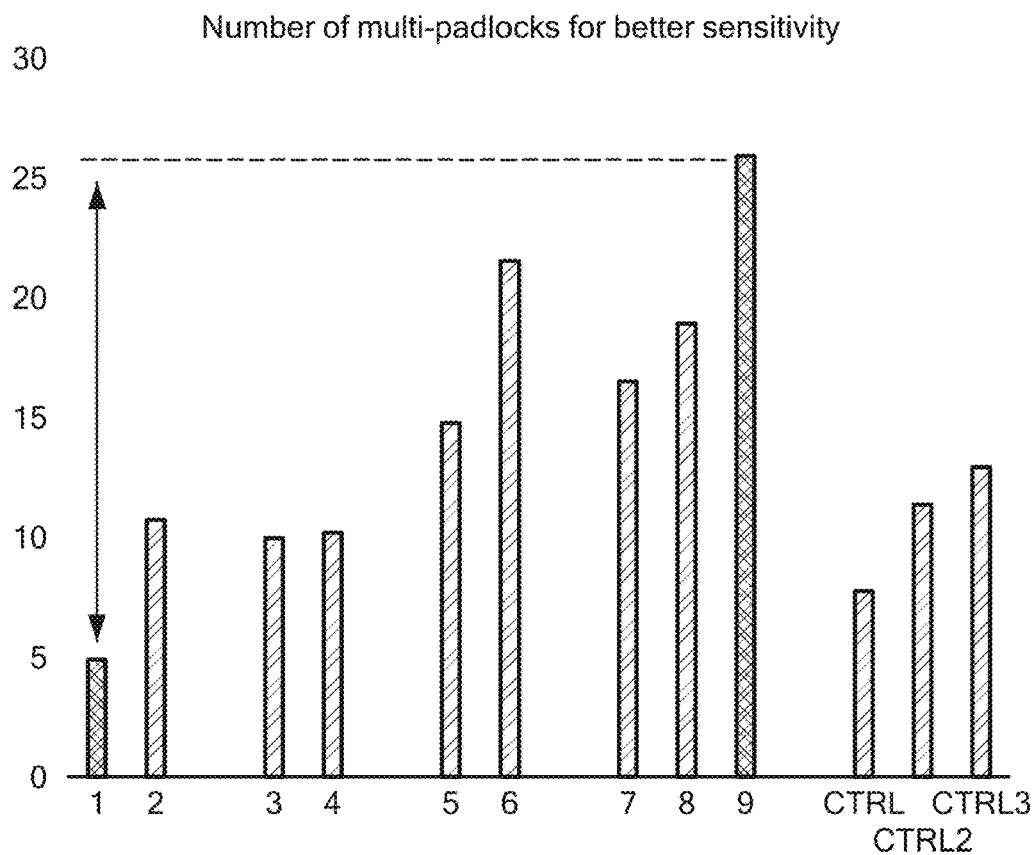
FIG. 8C shows the concentration of ligated DNA padlock probe as a function of the number of padlock probes (each present at 10 ng/mL, RNA target present at 10 ng/mL).
Figure 8D:
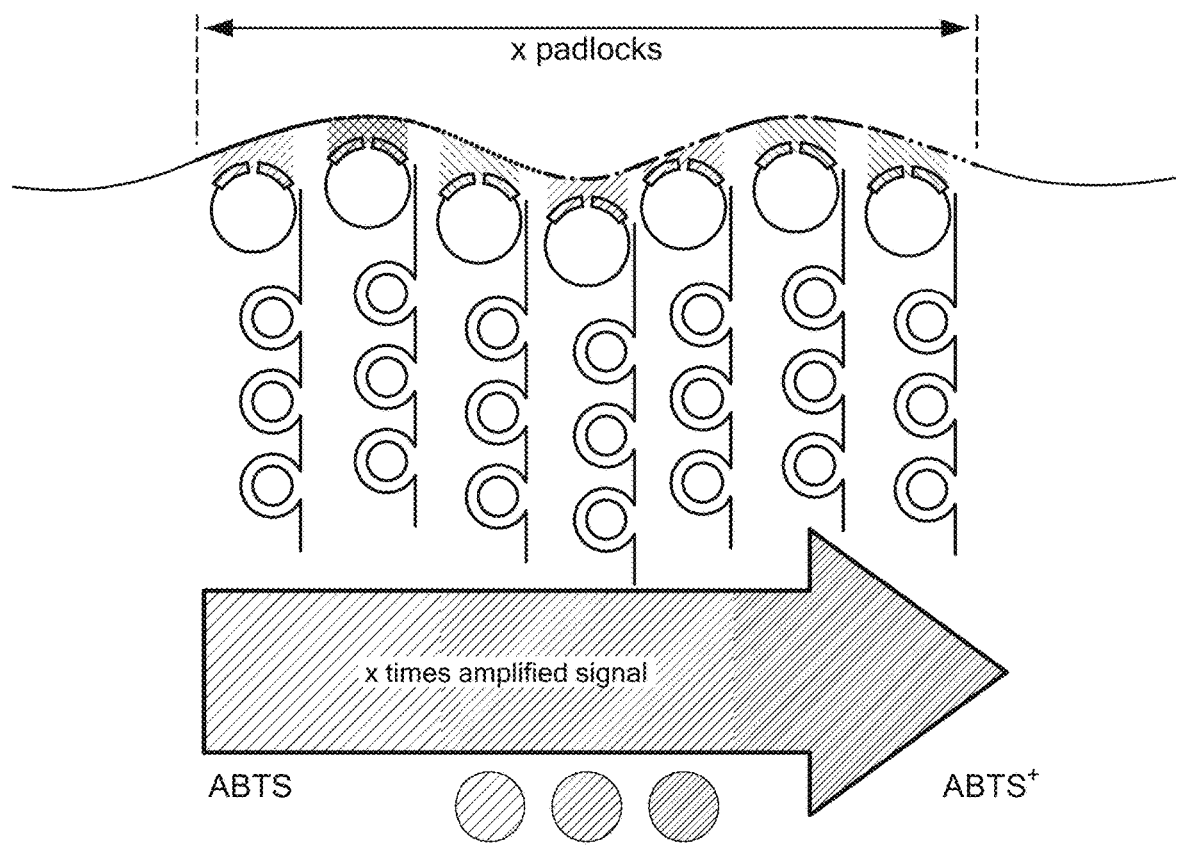
FIG. 8D shows schematically how the use of multiple padlock probes directed to different target sequences of a target nucleic acid molecule can multiply the amount of colored product and increase sensitivity.
Figure 8E:
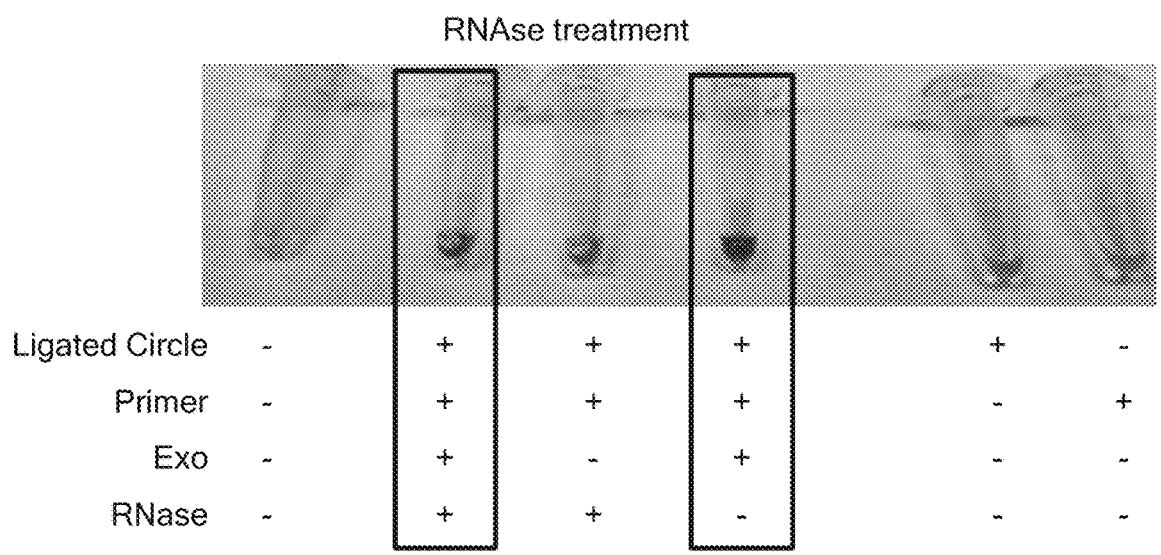
FIG. 8E shows the results of an experiment to determine the effect of added exonuclease on the amount of colored product from an RCA reaction.
Figure 8F:
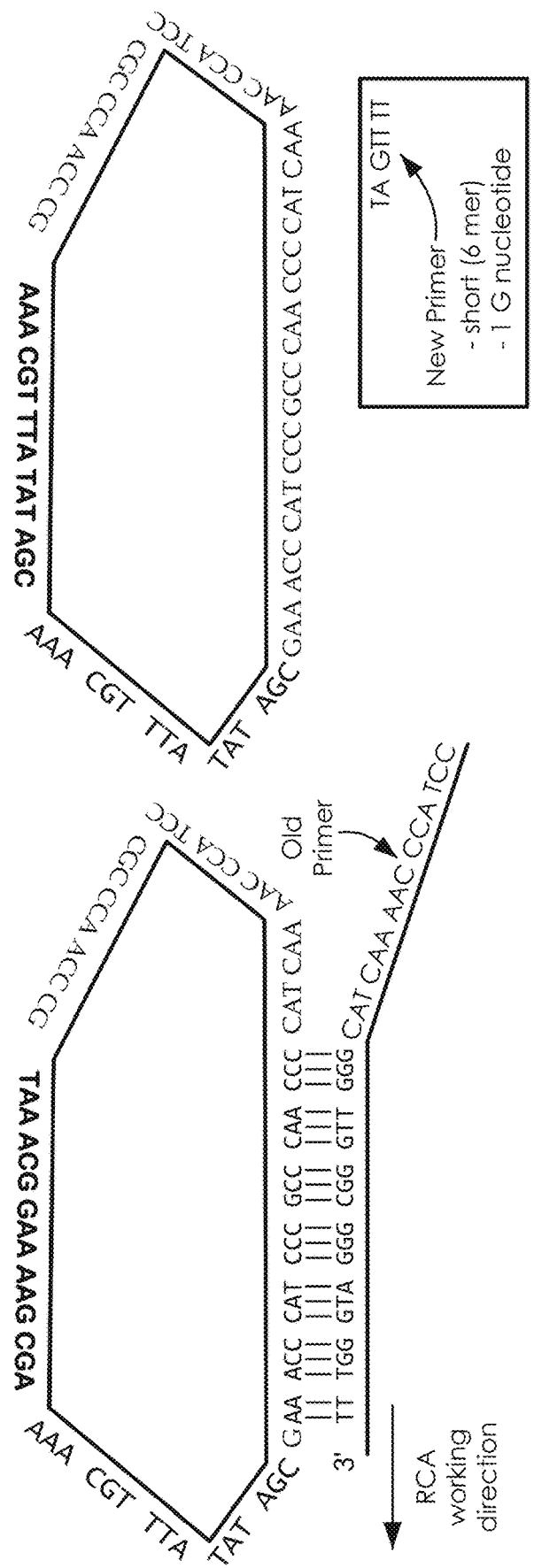
FIG. 8F shows the result of optimization of the padlock binding sequence of an RCA initiation primer and the corresponding primer binding sequence of the padlock probe. The old primer is SEQ ID NO:19, and the new primer is SEQ ID NO:20.
Figure 10A:
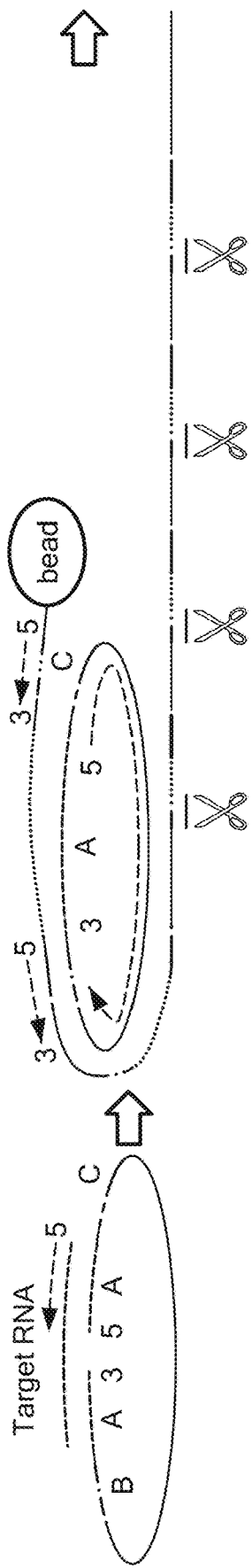
FIGS. 10A-10E depict consecutive amplification cycles of a circle-to-circle (C2C) RCA process for detecting the presence, absence, or amount of a target nucleic acid molecule. In the first cycle of FIG. 10A, a padlock probe is hybridized to a target sequence of a target RNA molecule, ligated, and used to extend an RCA initiation primer. The padlock probe contains a restriction enzyme cleavage sequence (C) for use in separating copies of the padlock from the amplified product In the second amplification of FIG. 10B, the amplified copies of the first padlock probe are hybridized to a C2C primer, ligated, amplified, and then separated using the restriction enzyme and restriction primer. Further amplification cycles can be carried out (see FIGS. 10C-10E, thereby increasing the number of copies of the detection sequence (even numbered cycles) and its complement (odd numbered cycles).
Figure 10B:
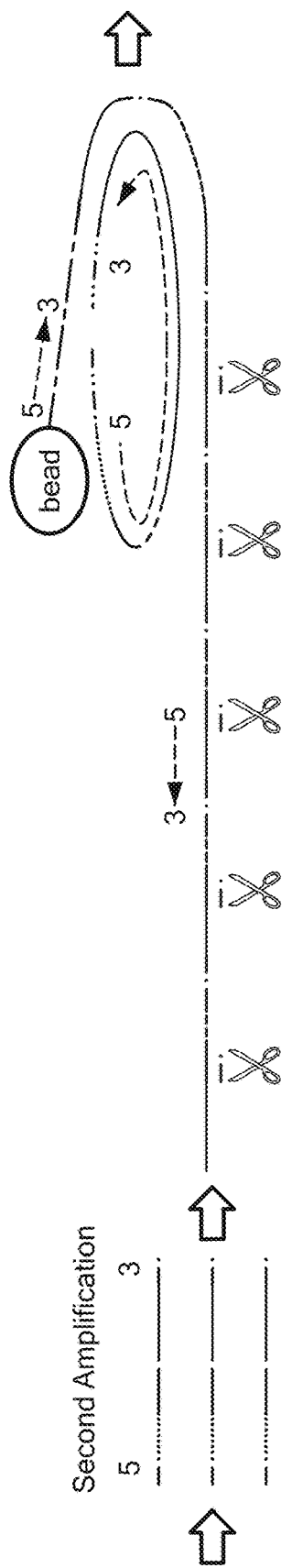
Figure 10C:
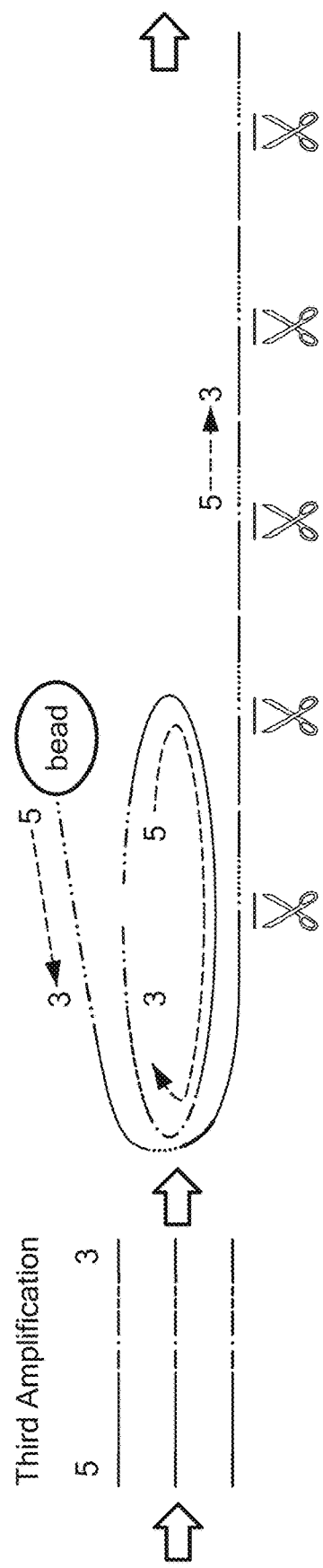
Figure 10D:
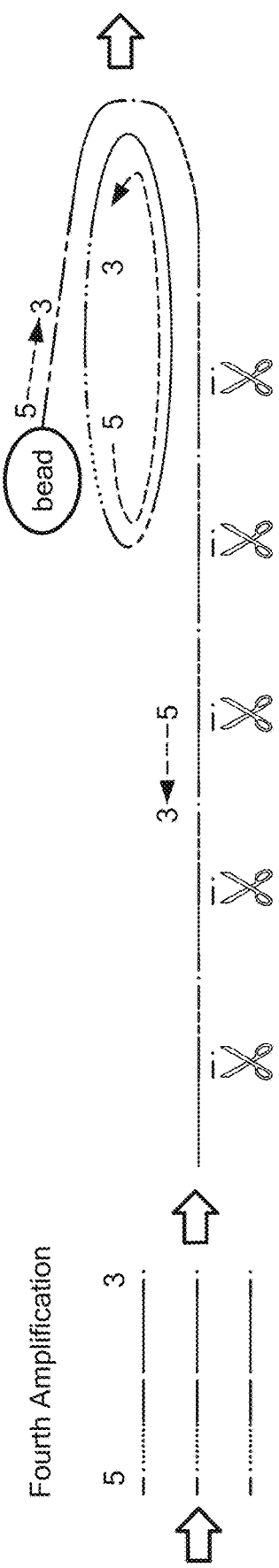
Figure 10E:
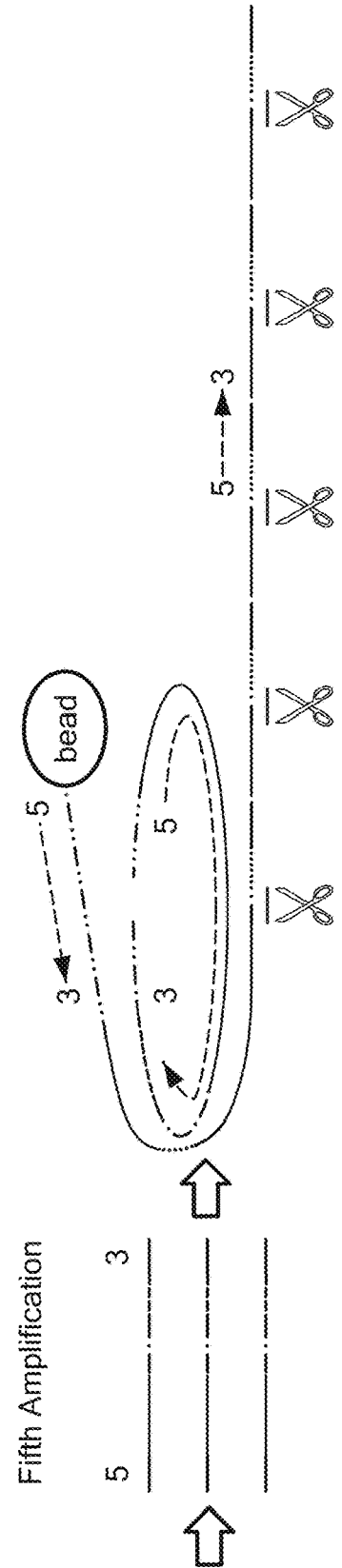

FIGS. 8A-8F illustrate optimization of several parameters of the present technology in order to improve sensitivity or specificity and reduce analysis time. FIG. 8A shows that DNA yield from the RCA ligase reaction can be improved by using a target sequence length of about 30 nucleotide bases, with shorter targets reducing ligation efficiency. FIG. 8B shows that ligation time, which is a time-consuming step of RCA due to enzyme kinetics, can be sufficient at 60 minutes, with longer incubation times not improving results, and shorter incubation times providing lower yields of ligated DNA. FIG. 8C confirms that increasing the number of padlocks (and target sequences) for a single target nucleic acid molecule dramatically improves yield of ligated DNA. Increasing the number of padlock probes from 1 to 9 increased ligated DNA 5-fold. FIG. 8D schematically illustrates the principle that increasing the number of multiple padlocks on a single target nucleic acid molecule has a multiplier effect. The experiment summarized in FIG. 8E showed that inclusion of an exonuclease enzyme, often used in RCA methodology, did not improve results, suggesting that this component and reaction step can be omitted to save time and cost. Finally, the experiment summarized in FIG. 8F showed that the RCA initiation primer can be reduced in length from an often used length of 15 nucleotide bases and a sequence requiring several guanine nucleotides in the padlock probe to a shorter 6-7 nucleotides and a sequence requiring only a single guanine nucleotide in the padlock probe. This increased sensitivity by reducing background caused by the several G bases in the previously used padlocks when using GQ-DNA based colorimetry. These are merely examples of the optimizations possible to optimize RCA for use in ultrasensitive detection of nucleic acid molecules.

FIG. 9 presents a set of 21 DNA sequences for padlock probes directed to different target sequences within SARS-CoV-2 RNA. The set of probes shares a common primer binding sequence and a common detection sequence, which is designed for GQ-DNA based colorimetric detection. The analysis of reaction kinetics discussed above leads to a 21-fold increase in sensitivity for SARS-CoV-2 RNA detection compared to use of a single padlock and target sequence. Different combinations of these probe sequences also can be used as sets for SARS-CoV-2 RNA detection, such as any 2 or more, any 3 or more, any 4 or more, any 5 or more, any 6 or more, any 7 or more, any 8 or more, any 9 or more, any 10 or more, any 11 or more, any 12 or more, any 13 or more, any 14 or more, any 15 or more, any 16 or more, any 17 or more, any 18 or more, any 19 or more, or any 20 of the 21 sequences shown in FIG. 9.

A variation of RCA methodology that can also be used to substantially enhance sensitivity is circle-to-circle (C2C) RCA, as diagramed in FIGS. 10A-10E. In the first cycle, shown in FIG. 10A, a padlock probe is hybridized to a target sequence of a target RNA molecule, ligated, and used to extend an RCA initiation primer. The process is similar to standard RCA at this point, except that the padlock probe contains a restriction enzyme cleavage sequence which is used to separate copies of the complement of the padlock probe from the extended product resulting from the first round of RCA. In the second amplification or cycle, shown in FIG. 10B, the amplified copies of the first padlock probe are hybridized to a C2C primer (which replaces the RCA initiation primer used to start the first cycle), ligated, amplified, and then separated using the restriction enzyme and restriction primer. The C2C primer differs from the RCA initiation primer in using the restriction enzyme cleavage site as a circularized probe binding site. Once the separated copies from the first cycle are separated, they can hybridize with the C2C primer, become ligated, and serve as template for the second C2C RCA cycle. Further amplification cycles can be carried out in a manner similar to the second cycle so as to obtain an increased number copies of the detection sequence, or its complement. See FIGS. 10C-10E. The C2C process can be facilitated by conjugating both the RCA initiation primer and the C2C primer to a set of microbeads, preferably with each microbead conjugated to both primers at a 1:1 weight ratio or molar ratio of RCA initiation primer to C2C primer.

The combined use of multiple padlock probes binding to multiple target sequences of a single target nucleic acid molecule plus the use of C2C RCA can provide an increase in sensitivity of detection of several orders of magnitude, such as a sensitivity increase of 10-fold, 100-fold, 1000-fold, 10000-fold or more, compared to use of standard RCE and a single padlock probe and target sequence.

In order to use multiplex detection of different target nucleic acid molecules, such as different viral RNAs, in a single assay, the assay must include for each target a separate set of RCA initiation primers and matched padlock probes. The RCA initiation primers and padlock probes share complementary sequences that allow the circularized primers to bind and elongate the primer during the elongation/amplification step. Further, the padlock probes for a given target share a common detection sequence, giving rise to a unique and distinguishable detection signal different from those signaling the presence of other targets. However, when appropriately combined, the two or more sets of RCA primers and matched padlock probe sets can be used to simultaneously analyze a single sample, or multiple samples in a suitable device, for the presence, absence, or amount of two or more nucleic acid target molecules, which may represent different pathogens (e.g., different but related viral strains or viruses producing common symptoms). The number of different targets that can be simultaneously analyzed is typically limited by the number of independent detections that can be carried out in a single analysis, such as the number of different colored reaction products that can be detected by colorimetry or spectrophotometry, or the number of different fluorophores or combinations of fluorophores that can be simultaneously detected. A much higher number of different targets can be evaluated if the detection sequence is used as a DNA barcode; however, nucleic acid sequencing of the products is then required, which can increase the time for analysis.

The use of primer-conjugated microbeads or other solid supports can be very convenient when performing multiplexed assays. Different types of beads, or segregated solid support surface, can be conjugated with different RCA primers, one set of primers specific for each RNA to be detected. The different beads or surfaces can be coded by color or form for ease of use and for detection purposes.

Different detection modalities also can be used simultaneously during multiplex analysis, with different detections used for each target molecule analyzed. The type or location of beads or other solid supports can inform the user as to the type of detection to employ. For instance, with an influenza virus RNA as a first target and a SARS-CoV-2 RNA as a second target, these viruses can be detected separately and simultaneously by a fluorescence measurement in which different fluorophores are used for each target.

The present technology can provide rapid, highly sensitive, high throughput, accurate, and flexible diagnosis for use in a pandemic caused by a newly discovered virus or other pathogen. However, it also can be used in other types of diagnostics, including detection of DNA or RNA fragments, detection of mutants and genetic variants and their spread (both environmental or population spread and spread within an organism, such as for cancer cells), and detection of cellular RNA expression. The technology also can be used to analyze the presence of bacteria, including novel bacterial species, in environmental samples or in the food chain.

```

What is claimed is:

1. A method of determining a presence, absence, or amount of a target nucleic acid molecule in a sample, the method comprising the steps of:

(a) providing (i) the target nucleic acid molecule, which comprises at least one target sequence, (ii) an RCA initiation primer, (iii) five or more padlock probes; and (iv) nucleic acid ligase and polymerase enzymes;

wherein, each padlock probe comprises (1) a target binding sequence consisting of a pair of sequences complementary to adjacent portions of one of said target sequence, the pair forming termini of the padlock probe; (2) a primer binding sequence that is complementary to a padlock binding sequence of the RCA initiation primer; and (3) a detection sequence comprising a G-quadruplex DNAzyme;

wherein the RCA initiation primer comprises said padlock binding sequence;

(b) hybridizing the padlock probe with the target sequence and ligating the termini of the padlock probe using the ligase to form a circular single-stranded nucleic acid molecule;

(c) hybridizing the circular single-stranded nucleic acid molecule to the RCA initiation primer;

(d) extending the RCA initiation primer using the polymerase and the hybridized circular single-stranded nucleic acid molecule to form a single-stranded nucleic acid product comprising a plurality of detection sequence copies;

(e) forming a hemin complex with the G-quadruplex DNAzyme of the detection sequence copies and using the complex to form a colored or fluorescent product; and (f) determining by detection of the colored or fluorescent product a presence, absence, or amount of the colored or fluorescent product resulting from step (e), wherein presence of the product indicates presence of the target nucleic acid molecule in the sample, absence of the product indicates absence of the nucleic acid molecule in the sample, and detection of an amount of the product indicates an amount of the target nucleic acid molecule in the sample.

2. The method of claim 1, wherein at least 10 padlock probes are used, each of the padlock probes comprising a target binding sequence complementary to a different target sequence of the target nucleic acid molecule.

3. The method of claim 2, wherein at least 50 padlock probes are used, each of the padlock probes comprising a target binding sequence complementary to a different target sequence of the target nucleic acid molecule.

4. The method of claim 1, wherein the RCA reaction is circle-to-circle (C2C) RCA and further comprises, between steps (c) and (d), the steps of:

(c1) providing a plurality of C2C RCA primers that each comprise a sequence complementary to the RCA initiation primer;

(c2) fragmenting the single-stranded nucleic acid product using a restriction enzyme and restriction primer to obtain a plurality of linearized first circle products, each comprising the detection sequence or a complement thereof;

(c3) hybridizing the linearized first circle products to the C2C RCA primers and ligating the linearized first circle products using the ligase to form first circle products hybridized to the C2C RCA primers;

(c4) extending the C2C RCA primers using the polymerase and the first circle products to obtain second single-stranded nucleic acid products;

(c5) fragmenting the second single-stranded nucleic acid product using said restriction enzyme and restriction primer to obtain a plurality of linearized second circle products comprising the detection sequence or a complement thereof;

(c6) hybridizing the linearized second circle products to RCA initiation primers and ligating the linearized second circle products using the ligase to form second circle products hybridized to the RCA initiation primers; and proceeding to step (d), or optionally (c7) extending the RCA initiation primers using the polymerase and the second circle products to obtain further single-stranded nucleic acid products, each product comprising a plurality of detection sequences or complements thereof, and repeating steps (c2)-(c6).

5. The method of claim 1, wherein the target nucleic acid molecule is an RNA molecule from SARS-CoV-2 or from a SARS-CoV-2 infected cell, and each said padlock probe comprises a sequence of at least 20 consecutive nucleotides complementary to any portion of said RNA molecule.

6. The method of claim 5, further comprising determining a presence, absence, or amount of a second target nucleic acid molecule using steps (a) through (e), and wherein the second target nucleic acid molecule is from an influenza strain or a second SARS-CoV-2 strain.

7. The method of claim 1, wherein the target nucleic acid molecule comprises at least 100 target sequences, and wherein at least 100 padlock probes are used, each of the padlock probes comprising a target binding sequence complementary to a different one of said at least 100 target sequences of the target nucleic acid molecule.

8. The method of claim 1, wherein the target nucleic acid molecule is from a virus selected from the group consisting of SARS-CoV-2, SARS, MERS, influenza, and ebola.

9. The method of claim 1 that is carried out using a microfluidic device, an array, a microwell plate, one or more tubes, or using a paperfluidic format.

10. The method of claim 1, wherein the RCA initiation primer is coupled to a solid support selected from the group consisting of microbeads, a glass surface, a polymer surface, a paper surface, and a surface in a tube, a chip, a microwell plate, or a microfluidic device.

11. The method of claim 1 that is capable of detecting an amount of said target nucleic acid molecule in the femtomole range or in the attomole range.

12. The method of claim 1 that is used for detection of a viral infection in a subject by detecting the presence of said target nucleic acid molecule in a sample from the subject.

13. The method of claim 12, wherein the viral infection is COVID-19.

14. The method of claim 12 that is used to identify which viral infection a subject has by determining simultaneously the presence, absence, or amount of two or more different target nucleic acid molecules, each nucleic acid molecule specifically identifying a different virus.

* * * * *

                          SEQUENCE LISTING

<160> NUMBER OF SEQ ID NOS: 51

<210> SEQ ID NO 1
<211> LENGTH: 34
<212> TYPE: DNA
<213> ORGANISM: Artificial sequence
<220> FEATURE:
<223> OTHER INFORMATION: Detection sequence

<400> SEQUENCE: 1
aaaaaaacgc gaaaaaaaac gcgcgaaaaa aacg                              34

<210> SEQ ID NO 2
<211> LENGTH: 32
<212> TYPE: DNA
<213> ORGANISM: Artificial Sequence
<220> FEATURE:
<223> OTHER INFORMATION: Detection sequence

<400> SEQUENCE: 2 ggggggata tggggggggg atatgggggg gg                                 32

<210> SEQ ID NO 3
<211> LENGTH: 117
<212> TYPE: DNA
<213> ORGANISM: SARS-CoV-2

<400> SEQUENCE: 3
atgggctata taaacgtttt cgcttttccg tttacgatat atagtctact cttgtgcaga    60
atgaattctc gtaactacat agcacaagta gatgtagtta actttaatct cacatag      117
```

```
<210> SEQ ID NO 4
<211> LENGTH: 117
<212> TYPE: RNA
<213> ORGANISM: SARS-CoV-2

<400> SEQUENCE: 4
augggcuaua uaaacguuuu cgcuuuuccg uuuacgauau auagucuacu cuugugcaga        60
augaauucuc guaacuacau agcacaagua gauguaguua acuuuaaucu cacauag         117

<210> SEQ ID NO 5
<211> LENGTH: 30
<212> TYPE: DNA
<213> ORGANISM: SARS-CoV-2

<400> SEQUENCE: 5
gctatataaa cgttttcgct tttccgttta                                        30

<210> SEQ ID NO 6
<211> LENGTH: 30
<212> TYPE: DNA
<213> ORGANISM: Artificial Sequence
<220> FEATURE:
<223> OTHER INFORMATION: Target binding sequence

<400> SEQUENCE: 6
cgatatattt gcaaaagcga aaaggcaaat                                        30

<210> SEQ ID NO 7
<211> LENGTH: 45
<212> TYPE: DNA
<213> ORGANISM: Artificial sequence
<220> FEATURE:
<223> OTHER INFORMATION: Padlock probe fragment
<220> FEATURE:
<221> NAME/KEY: misc_feature
<222> LOCATION: (16)..(30)
<223> OTHER INFORMATION: n is a, c, g, or t

<400> SEQUENCE: 7
taaacggaaa agcgannnnn nnnnnnnnnn aaacgtttat atagc                       45

<210> SEQ ID NO 8
<211> LENGTH: 30
<212> TYPE: DNA
<213> ORGANISM: SARS-CoV-2

<400> SEQUENCE: 8
agtctactct tgtgcagaat gaattctcgt                                        30

<210> SEQ ID NO 9
<211> LENGTH: 30
<212> TYPE: DNA
<213> ORGANISM: Artificial sequence
<220> FEATURE:
<223> OTHER INFORMATION: Target binding sequence

<400> SEQUENCE: 9
tcagatgaga acacgtctta cttaagagca                                        30

<210> SEQ ID NO 10
<211> LENGTH: 45
<212> TYPE: DNA
<213> ORGANISM: Artificial sequence
<220> FEATURE:
<223> OTHER INFORMATION: Padlock probe fragment
```

```
<220> FEATURE:
<221> NAME/KEY: misc_feature
<222> LOCATION: (16)..(30)
<223> OTHER INFORMATION: n is a, c, g, or t

<400> SEQUENCE: 10
acgagaattc attctnnnnn nnnnnnnnnn gcacaagagt agact           45

<210> SEQ ID NO 11
<211> LENGTH: 30
<212> TYPE: DNA
<213> ORGANISM: SARS-CoV-2

<400> SEQUENCE: 11
agcacaagta gatgtagtta actttaatct                            30

<210> SEQ ID NO 12
<211> LENGTH: 30
<212> TYPE: DNA
<213> ORGANISM: Artificial sequence
<220> FEATURE:
<223> OTHER INFORMATION: Target binding sequence

<400> SEQUENCE: 12
tcgtgttcat ctacatcaat tgaaattaga                            30

<210> SEQ ID NO 13
<211> LENGTH: 45
<212> TYPE: DNA
<213> ORGANISM: Artificial sequence
<220> FEATURE:
<223> OTHER INFORMATION: Padlock probe fragment
<220> FEATURE:
<221> NAME/KEY: misc_feature
<222> LOCATION: (16)..(30)
<223> OTHER INFORMATION: n is a, c, g, or t

<400> SEQUENCE: 13
agattaaagt taactnnnnn nnnnnnnnnn acatctactt gtgct           45

<210> SEQ ID NO 14
<211> LENGTH: 35
<212> TYPE: DNA
<213> ORGANISM: Artificial sequence
<220> FEATURE:
<223> OTHER INFORMATION: RCA initiation primer

<400> SEQUENCE: 14
tttgggtagg gcgggttggg catcaaaacc catcc                      35

<210> SEQ ID NO 15
<211> LENGTH: 77
<212> TYPE: DNA
<213> ORGANISM: Artificial sequence
<220> FEATURE:
<223> OTHER INFORMATION: Padlock probe

<400> SEQUENCE: 15
taaacggaaa agcgagaaac ccatcccgcc caacccatc aaaacccatc ccgcccaacc   60
cgaaacgttt atatagc                                          77

<210> SEQ ID NO 16
<211> LENGTH: 76
<212> TYPE: DNA
<213> ORGANISM: Artificial sequence
```

```
<220> FEATURE:
<223> OTHER INFORMATION: Padlock probe

<400> SEQUENCE: 16
acgagaattc attcgaaacc catcccgccc aaccccatca aaacccatcc cgcccaaccc     60
ggcacaagag tagact                                                   76

<210> SEQ ID NO 17
<211> LENGTH: 77
<212> TYPE: DNA
<213> ORGANISM: Artificial sequence
<220> FEATURE:
<223> OTHER INFORMATION: Padlock  probe

<400> SEQUENCE: 17
agattaaagt taactgaaac ccatcccgcc caaccccatc aaaacccatc cgcccaacc     60 cgacatctac ttgtgct                                                  77

<210> SEQ ID NO 18
<211> LENGTH: 47
<212> TYPE: DNA
<213> ORGANISM: Artificial sequence
<220> FEATURE:
<223> OTHER INFORMATION: Detection sequence

<400> SEQUENCE: 18
gaaacccatc ccgcccaacc ccatcaaaac ccatcccgcc caacccg                 47

<210> SEQ ID NO 19
<211> LENGTH: 35
<212> TYPE: DNA
<213> ORGANISM: Artificial sequence
<220> FEATURE:
<223> OTHER INFORMATION: RCA initiation primer

<400> SEQUENCE: 19
tttggctagg gcgggttggg catcaaaacc catcc                              35

<210> SEQ ID NO 20
<211> LENGTH: 27
<212> TYPE: DNA
<213> ORGANISM: Artificial sequence
<220> FEATURE:
<223> OTHER INFORMATION: RCA initiation primer

<400> SEQUENCE: 20
tttggctagg gcgggttggg tagtttt                                       27

<210> SEQ ID NO 21
<211> LENGTH: 100
<212> TYPE: DNA
<213> ORGANISM: SARS-CoV-2

<400> SEQUENCE: 21
tgagttatga ggatcaagat gcacttttcg catatacaaa acgtaatgtc atccctacta   60
taactcaaat gaatcttaag tatgccatta gtgcaaagaa                        100

<210> SEQ ID NO 22
<211> LENGTH: 77
<212> TYPE: DNA
<213> ORGANISM: Artificial sequence
<220> FEATURE:
<223> OTHER INFORMATION: Padlock probe
```

-continued

<400> SEQUENCE: 22
agtgcatctt gatccgaaac ccatcccgcc caaccccatc aaaacccatc ccgcccaacc    60
cgtttgtata tgcgaaa                                                   77

<210> SEQ ID NO 23
<211> LENGTH: 77
<212> TYPE: DNA
<213> ORGANISM: Artificial sequence
<220> FEATURE:
<223> OTHER INFORMATION: Padlock probe

<400> SEQUENCE: 23
gattcatttg agttagaaac ccatcccgcc caaccccatc aaaacccatc ccgcccaacc    60
cgtaatggca tacttaa                                                   77

<210> SEQ ID NO 24
<211> LENGTH: 100
<212> TYPE: DNA
<213> ORGANISM: SARS-CoV-2

<400> SEQUENCE: 24
tagagctcgc accgtagctg gtgtctctat ctgtagtact atgaccaata gacagtttca    60
tcaaaaatta ttgaaatcaa tagccgccac tagaggagct                         100

<210> SEQ ID NO 25
<211> LENGTH: 77
<212> TYPE: DNA
<213> ORGANISM: Artificial sequence
<220> FEATURE:
<223> OTHER INFORMATION: Padlock probe

<400> SEQUENCE: 25
gacaccagct acggtgaaac ccatcccgcc caaccccatc aaaacccatc ccgcccaacc    60
cgagtactac agataga                                                   77

<210> SEQ ID NO 26
<211> LENGTH: 77
<212> TYPE: DNA
<213> ORGANISM: Artificial sequence
<220> FEATURE:
<223> OTHER INFORMATION: Padlock probe

<400> SEQUENCE: 26
ttcaataatt tttgagaaac ccatcccgcc caaccccatc aaaacccatc ccgcccaacc    60
cggtggcggc tattgat                                                   77

<210> SEQ ID NO 27
<211> LENGTH: 87
<212> TYPE: DNA
<213> ORGANISM: SARS-CoV-2

<400> SEQUENCE: 27
actgtagtaa ttggaacaag caaattctat ggtggttggc acaacatgtt aaaaactgtt    60
tatagtgatg tagaaaaccc tcacctt                                        87

<210> SEQ ID NO 28
<211> LENGTH: 77
<212> TYPE: DNA
<213> ORGANISM: Artificial sequence
<220> FEATURE:
<223> OTHER INFORMATION: Padlock probe

```
<400> SEQUENCE: 28
ctataaacag tttttgaaac ccatcccgcc caaccccatc aaacccatc cgcccaacc        60 cggggttttc tacatca                                                    77

<210> SEQ ID NO 29
<211> LENGTH: 77
<212> TYPE: DNA
<213> ORGANISM: Artificial sequence
<220> FEATURE:
<223> OTHER INFORMATION: Padlock probe

<400> SEQUENCE: 29
gcgcagtaag gatgggaaac ccatcccgcc caaccccatc aaacccatc cgcccaacc        60 cgacgcacac aatcgaa                                                    77

<210> SEQ ID NO 30
<211> LENGTH: 107
<212> TYPE: DNA
<213> ORGANISM: SARS-CoV-2

<400> SEQUENCE: 30
aatgtctatg cagattcatt tgtaattaga ggtgatgaag tcagacaaat cgctccaggg      60
caaactggaa agattgctga ttataattat aaattaccag atgattt                  107

<210> SEQ ID NO 31
<211> LENGTH: 80
<212> TYPE: DNA
<213> ORGANISM: Artificial sequence
<220> FEATURE:
<223> OTHER INFORMATION: Padlock probe

<400> SEQUENCE: 31
atctgcatag acattgaaac ccatcccgcc caaccccatc aaacccatc cgcccaacc        60 cgtaatctaa ttacaaatga                                                 80

<210> SEQ ID NO 32
<211> LENGTH: 80
<212> TYPE: DNA
<213> ORGANISM: Artificial sequence
<220> FEATURE:
<223> OTHER INFORMATION: Padlock probe

<400> SEQUENCE: 32
agcgatttgt ctgacgaaac ccatcccgcc caaccccatc aaacccatc cgcccaacc        60 cgtaatccag tttgccctgg                                                 80

<210> SEQ ID NO 33
<211> LENGTH: 80
<212> TYPE: DNA
<213> ORGANISM: Artificial sequence
<220> FEATURE:
<223> OTHER INFORMATION: Padlock probe

<400> SEQUENCE: 33
ttataattat aatcagaaac ccatcccgcc caaccccatc aaacccatc cgcccaacc        60 cgtaaaaatc atctggtaat                                                 80

<210> SEQ ID NO 34
<211> LENGTH: 120
<212> TYPE: DNA
<213> ORGANISM: SARS-CoV-2
```

-continued

<400> SEQUENCE: 34
atggcagatt ccaacggtac tattaccgtt gaagagctta aaaagctcct tgaacaatgg     60
aacctagtaa taggtttcct attccttaca tggatttgtc ttctacaatt tgcctatgcc    120

<210> SEQ ID NO 35
<211> LENGTH: 80
<212> TYPE: DNA
<213> ORGANISM: Artificial sequence
<220> FEATURE:
<223> OTHER INFORMATION: Padlock probe

<400> SEQUENCE: 35
gttggaatct gccatgaaac ccatcccgcc caaccccatc aaaacccatc ccgcccaacc     60
cgtaaaacgg taatagtacc                                                80

<210> SEQ ID NO 36
<211> LENGTH: 80
<212> TYPE: DNA
<213> ORGANISM: Artificial sequence
<220> FEATURE:
<223> OTHER INFORMATION: Padlock probe

<400> SEQUENCE: 36
ccattgttca aggaggaaac ccatcccgcc caaccccatc aaaacccatc ccgcccaacc     60
cgtaaaccta ttactaggtt                                                80

<210> SEQ ID NO 37
<211> LENGTH: 80
<212> TYPE: DNA
<213> ORGANISM: Artificial sequence
<220> FEATURE:
<223> OTHER INFORMATION: Padlock probe

<400> SEQUENCE: 37
tagaagacaa atccagaaac ccatcccgcc caaccccatc aaaacccatc ccgcccaacc     60
cgtaaggcat aggcaaattg                                                80

<210> SEQ ID NO 38
<211> LENGTH: 120
<212> TYPE: DNA
<213> ORGANISM: SARS-CoB-2

<400> SEQUENCE: 38
aacaggaata ggttttttgta tataattaag ttaattttcc tctggctgtt atggccagta     60
actttagctt gttttgtgct tgctgctgtt tacagaataa attggatcac cggtggaatt    120

<210> SEQ ID NO 39
<211> LENGTH: 80
<212> TYPE: DNA
<213> ORGANISM: Artificial sequence
<220> FEATURE:
<223> OTHER INFORMATION: Padlock probe

<400> SEQUENCE: 39
aaacctattc ctgttgaaac ccatcccgcc caaccccatc aaaacccatc ccgcccaacc     60
cgtaacttaa ttatatacaa                                                80

<210> SEQ ID NO 40
<211> LENGTH: 80
<212> TYPE: DNA
<213> ORGANISM: Artificial sequence

```
<220> FEATURE:
<223> OTHER INFORMATION: Padlock probe

<400> SEQUENCE: 40
tactggccat aacaggaaac ccatcccgcc caacccatc aaaacccatc ccgcccaacc    60
cgtaaaaaac aagctaaagt                                              80

<210> SEQ ID NO 41
<211> LENGTH: 80
<212> TYPE: DNA
<213> ORGANISM: Artificial sequence
<220> FEATURE:
<223> OTHER INFORMATION: Padlock probe

<400> SEQUENCE: 41
ccaatttatt ctgtagaaac ccatcccgcc caacccatc aaaacccatc ccgcccaacc    60
cgtaaaattc caccggtgat                                              80

<210> SEQ ID NO 42
<211> LENGTH: 120
<212> TYPE: DNA
<213> ORGANISM: SARS-CoV-2

<400> SEQUENCE: 42
gctatcgcaa tggcttgtct tgtaggcttg atgtggctca gctacttcat tgcttctttc    60
agactgtttg cgcgtacgcg ttccatgtgg tcattcaatc cagaaactaa cattcttctc   120

<210> SEQ ID NO 43
<211> LENGTH: 80
<212> TYPE: DNA
<213> ORGANISM: Artificial sequence
<220> FEATURE:
<223> OTHER INFORMATION: Padlock probe

<400> SEQUENCE: 43
agccattgcg atagcgaaac ccatcccgcc caacccatc aaaacccatc ccgcccaacc    60
cgtaacaagc ctacaagaca                                              80

<210> SEQ ID NO 44
<211> LENGTH: 80
<212> TYPE: DNA
<213> ORGANISM: Artificial sequence
<220> FEATURE:
<223> OTHER INFORMATION: Padlock probe

<400> SEQUENCE: 44
gaaagaagca atgaagaaac ccatcccgcc caacccatc aaaacccatc ccgcccaacc    60
cgtaaacgcg caaacagtct                                              80

<210> SEQ ID NO 45
<211> LENGTH: 80
<212> TYPE: DNA
<213> ORGANISM: Artificial sequence
<220> FEATURE:
<223> OTHER INFORMATION: Padlock probe

<400> SEQUENCE: 45
ttctggattg aatgagaaac ccatcccgcc caacccatc aaaacccatc ccgcccaacc    60
cgtaagagaa gaatgttagt                                              80
```

```
<210> SEQ ID NO 46
<211> LENGTH: 30
<212> TYPE: DNA
<213> ORGANISM: SARS-CoV-2

<400> SEQUENCE: 46
ctggcagtaa ccagaatgga gaacgcagtg                                      30

<210> SEQ ID NO 47
<211> LENGTH: 77
<212> TYPE: DNA
<213> ORGANISM: Artificial sequence
<220> FEATURE:
<223> OTHER INFORMATION: Padlock probe

<400> SEQUENCE: 47
tctggttact gccaggaaac ccatcccgcc caacccatc aaaacccatc ccgcccaacc      60
cgtttgtata tgcgaaa                                                    77

<210> SEQ ID NO 48
<211> LENGTH: 30
<212> TYPE: DNA
<213> ORGANISM: SARS-CoV-2

<400> SEQUENCE: 48
atcacattgg cacccgcaat cctgctaaca                                      30

<210> SEQ ID NO 49
<211> LENGTH: 77
<212> TYPE: DNA
<213> ORGANISM: Artificial sequence
<220> FEATURE:
<223> OTHER INFORMATION: Padlock probe

<400> SEQUENCE: 49
gggtgccaat gtgatgaaac ccatcccgcc caacccatc aaaacccatc ccgcccaacc      60
cgtgttagca ggattgc                                                    77

<210> SEQ ID NO 50
<211> LENGTH: 30
<212> TYPE: DNA
<213> ORGANISM: SARS-CoV-2

<400> SEQUENCE: 50
gaaattttgg ggaccaggaa ctaatcagac                                      30

<210> SEQ ID NO 51
<211> LENGTH: 77
<212> TYPE: DNA
<213> ORGANISM: Artificial sequence
<220> FEATURE:
<223> OTHER INFORMATION: Padlock probe

<400> SEQUENCE: 51
ggtccccaaa atttcgaaac ccatcccgcc caacccatc aaaacccatc ccgcccaacc      60
cggtctgatt agttcct                                                    77
```